(12) United States Patent
Kolodziejczyk et al.

(10) Patent No.: US 9,029,352 B2
(45) Date of Patent: May 12, 2015

(54) PROCESS FOR THE PREPARATION OF C-FMS KINASE INHIBITORS

(71) Applicant: Janssen Pharmaceutica NV, Beerse (BE)

(72) Inventors: Krzysztof Kolodziejczyk, Reading (GB); Alfred Elisabeth Stappers, Oud-Turnhout (BE); Christopher A. Teleha, Fort Washington, PA (US); Koen Johan Herman Weerts, Vosselaar (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/959,158

(22) Filed: Aug. 5, 2013

(65) Prior Publication Data

US 2014/0045789 A1 Feb. 13, 2014

Related U.S. Application Data

(60) Provisional application No. 61/660,446, filed on Aug. 7, 2012.

(51) Int. Cl.
  *C07F 7/10* (2006.01)
  *C07D 405/14* (2006.01)
  *C07D 309/30* (2006.01)

(52) U.S. Cl.
  CPC ............... *C07F 7/10* (2013.01); *C07D 405/14* (2013.01); *C07D 309/30* (2013.01)

(58) Field of Classification Search
  None
  See application file for complete search history.

(56) References Cited

U.S. PATENT DOCUMENTS

| | | | |
|---|---|---|---|
| 2,466,420 A | 4/1949 | Hagemeyer et al. |
| 3,226,394 A | 12/1965 | Schipper, E. |
| 4,551,540 A | 11/1985 | Hechenbleikner et al. |
| 5,190,541 A | 3/1993 | Abele et al. |
| 5,474,765 A | 12/1995 | Thorpe |
| 5,762,918 A | 6/1998 | Thorpe |
| 5,855,866 A | 1/1999 | Thorpe et al. |
| 5,874,442 A | 2/1999 | Doll et al. |
| 5,944,718 A | 8/1999 | Austin et al. |
| 5,968,952 A | 10/1999 | Venet et al. |
| 6,037,350 A | 3/2000 | Venet et al. |
| 6,100,254 A | 8/2000 | Budde et al. |
| 6,117,432 A | 9/2000 | Ganne et al. |
| 6,169,096 B1 | 1/2001 | Venet et al. |
| 6,187,786 B1 | 2/2001 | Venet et al. |
| 6,235,746 B1 | 5/2001 | Davis et al. |
| 6,342,219 B1 | 1/2002 | Thorpe et al. |
| 6,346,625 B1 | 2/2002 | Karabelas et al. |
| 6,383,790 B1 | 5/2002 | Shokat |
| 6,420,387 B1 | 7/2002 | Venet et al. |
| 6,458,800 B1 | 10/2002 | Angibaud et al. |
| 6,596,746 B1 | 7/2003 | Das et al. |
| 6,692,491 B1 | 2/2004 | Phan |
| 7,157,456 B2 | 1/2007 | Straub et al. |
| 7,208,493 B2 | 4/2007 | Wrasidlo et al. |
| 7,427,683 B2 | 9/2008 | Player et al. |
| 7,429,603 B2 | 9/2008 | Player et al. |
| 7,645,755 B2 | 1/2010 | Illig et al. |
| 7,662,837 B2 | 2/2010 | Illig et al. |
| 7,790,724 B2 | 9/2010 | Player et al. |
| 7,795,279 B2 | 9/2010 | Ballentine et al. |
| 7,973,035 B2 | 7/2011 | Illig et al. |
| 2002/0016625 A1 | 2/2002 | Falotico et al. |
| 2002/0019414 A1 | 2/2002 | Altmann et al. |
| 2003/0153610 A1 | 8/2003 | Straub et al. |
| 2004/0049032 A1 | 3/2004 | Charrier et al. |
| 2005/0113566 A1 | 5/2005 | Player et al. |
| 2005/0131022 A1 | 6/2005 | Player et al. |
| 2006/0040995 A1 | 2/2006 | Bacque et al. |
| 2006/0100619 A1 | 5/2006 | McClurken et al. |
| 2006/0122181 A1 | 6/2006 | Ikemoto et al. |
| 2006/0189623 A1 | 8/2006 | Illig et al. |
| 2006/0258724 A1 | 11/2006 | Straub et al. |
| 2006/0281788 A1 | 12/2006 | Baumann et al. |
| 2007/0249593 A1 | 10/2007 | Illig et al. |
| 2007/0249608 A1 | 10/2007 | Illig et al. |
| 2007/0249649 A1 | 10/2007 | Illig et al. |

(Continued)

FOREIGN PATENT DOCUMENTS

| | | |
|---|---|---|
| EP | 1566379 | 8/2005 |
| GB | 1189719 | 4/1970 |

(Continued)

OTHER PUBLICATIONS

Abarbri et al., J. Org. Chem. (2000), 65, 4618-4634.
Barkenbus et al., Journal of Organic Chemistry (1951), 16, 232-8.
Brown et al., J. Chem. Soc., Perkin Trans. 2, 1039-1051 (2002).
Byrn et al., Solid-State Chemistry of Drugs, Second Edition, 1999, pp. 233-247.
Crandall et al., J. Am. Chem. Soc. (1968), 90, 6251-6253.
Eastwood, P., Tetrahedron Lett. (2000), 41, 3705-8.
Gavezzotti, "Are Crystal Structures Predictable?" Accounts of Chemical Research, vol. 27, pp. 309-314 (1994).
Guillory (in Brittain ed.) Polymorphism, etc., NY: Marcel Dekker, Inc., 1999, 1-2, 183-226.

(Continued)

*Primary Examiner* — Timothy R Rozof

(57) ABSTRACT

The present invention is directed to a process for the preparation of heterocyclic derivatives of formula I

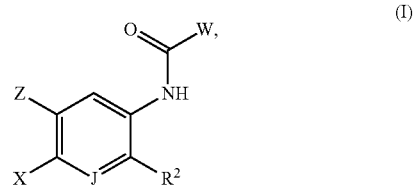

wherein J, X, Z, and $R^2$ are as defined herein. Such compounds are useful as protein tyrosine kinase inhibitors, more particularly inhibitors of c-fms kinase.

62 Claims, No Drawings

(56) References Cited

U.S. PATENT DOCUMENTS

| | | |
|---|---|---|
| 2008/0051402 A1 | 2/2008 | Illig et al. |
| 2009/0105296 A1 | 4/2009 | Illig et al. |
| 2009/0197913 A1 | 8/2009 | Baumann et al. |
| 2010/0174094 A1 | 7/2010 | Zierke et al. |
| 2011/0195960 A1 | 8/2011 | Illig et al. |

FOREIGN PATENT DOCUMENTS

| | | |
|---|---|---|
| WO | 94/10138 | 5/1994 |
| WO | 96/011932 | 4/1996 |
| WO | 96/21452 | 7/1996 |
| WO | 96/32907 | 10/1996 |
| WO | 97/16443 | 5/1997 |
| WO | 97/21701 | 6/1997 |
| WO | 97/30992 | 8/1997 |
| WO | 98/06700 | 2/1998 |
| WO | 98/28264 | 7/1998 |
| WO | 98/28303 | 7/1998 |
| WO | 98/40383 | 9/1998 |
| WO | 98/49157 | 11/1998 |
| WO | 98/54174 | 12/1998 |
| WO | 99/45712 | 9/1999 |
| WO | 99/45912 | 9/1999 |
| WO | 00/01691 | 1/2000 |
| WO | 00/02871 | 1/2000 |
| WO | WO 00/12498 | 3/2000 |
| WO | WO 00/12499 | 3/2000 |
| WO | 00/027820 | 5/2000 |
| WO | 02/068406 | 5/2000 |
| WO | WO 00/39082 | 7/2000 |
| WO | 01/047897 | 7/2001 |
| WO | 01/047919 | 7/2001 |
| WO | 01/49667 | 7/2001 |
| WO | WO 02/032861 A2 | 4/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A2 | 5/2003 |
| WO | WO 03/037347 A1 | 5/2003 |
| WO | WO 03/057690 A1 | 7/2003 |
| WO | 03/099796 | 12/2003 |
| WO | WO 03/099771 A2 | 12/2003 |
| WO | WO 2004/005281 A1 | 1/2004 |
| WO | WO 2004/016597 A2 | 2/2004 |
| WO | 2004/022525 | 3/2004 |
| WO | WO 2004/018419 A2 | 3/2004 |
| WO | WO 2004/039782 A1 | 5/2004 |
| WO | WO 2004/043389 A2 | 5/2004 |
| WO | WO 2004/046120 A2 | 6/2004 |
| WO | WO 2004/058749 A1 | 7/2004 |
| WO | 2004/085388 | 10/2004 |
| WO | 2004/096795 | 11/2004 |
| WO | 2005/012220 | 2/2005 |
| WO | WO 2005/040139 | 5/2005 |
| WO | WO 2005/047273 | 5/2005 |
| WO | 2005/073225 | 8/2005 |
| WO | 2006/047277 | 5/2006 |
| WO | 2006/047504 | 5/2006 |
| WO | 2006/135718 | 12/2006 |
| WO | 2006/138155 A1 | 12/2006 |
| WO | WO 2006/135630 | 12/2006 |
| WO | WO 2006/135636 | 12/2006 |
| WO | WO 2006/135713 | 12/2006 |
| WO | 2007/048088 | 4/2007 |
| WO | 2009/058968 | 5/2009 |

OTHER PUBLICATIONS

Harmata et al., Org. Lett. (2000), 2, 2703-2705.
Hess et al., J. Am. Chem. Soc. (1998), 120, 12310.
Hogermeier et al., Chem. Eur. J., 2007, 13, 2410.
Johnson et al., J. Org. Chem. (1970), 35(3), 584-592.
Kim et al., European Journal of Organic Chemistry (2000), 12, 2195-2201.
Larock, R.C., Comprehensive Organic Transformations, $2^{nd}$ Ed., Wiley-VCH, NY, (1999), pp. 996-1003.
Lee, K. And Cha, J. K., J. Amer. Chem. Soc., 123: 5590-5591 (2001).
Lipshutz et al., Tetrahedron Lett. (1988), 29, 3411-3414.
McBee et al., Journal of the American Chemical Society (1957), 79, 2323-5.
Meltzer et al., Bioorganic & Medicinal Chemistry (2002), 10(11) and 3583-3591.
Noyori et al., Org. React., 1983, 29, 163.
Regan et al., J. Med. Chem., 46: 4676-86 (2003).
Reinecke et al., Chemistry-A European Journal (1995), 1(6), 368-73.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Schmid et al., Helv. Chim. Acta. (1974), 57, 1883 [see English summary provided].
Sendelbach, et al, Journal of Organic Chemistry (1999), 64(10), 3398-3408.
Stille, J. K., Angew. Chem, Int. Ed. Engl., 25: 508-524 (1986).
Sundermeier, U., Doebler, C. and Beller, M., Modern Oxidation Methods, Baeckvall, J. (Ed.)., 1-20, Wiley-Verlag (2004) Weinheim, Germany (2004).
Takahashi, K., et al, Chem. Lett. (2000), 126-7.
Takaya et al., J Amer Chem Soc, (1978), 100(6), 1765-77.
West et al., J. Org. Chem (1993), 58, 6795-6803.
Wroblewski et al., Journal of the American Chemical Society (1996), 118, 10168-10174.
Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Ansari-Lari, A. et al., "FLT3 mutations in myeloid sarcoma" British Journal of Haematology. Sep. 2004,126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243-256 (Alan R. Liss, Inc. 1985).
Auewarakul et al., Ann Hematol, 85:108-112, 2006.
Baumann CA, Zeng L, Donatelli RR, Maroney AC. Development of a quantitative, high-throughput cell-based enzyme-linked immunosorbent assay for detection of colony-stimulating factor-1 receptor tyrosine kinase inhibitors. J Biochem Biophys Methods. 2004; 60:69-79.
Beller et al., Applied Homogeneous Catalysis with Organometallic Compounds, Cornils, B. And Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1977, 66(1): 1-19.
Bodansky, M. et al., "The Practice of Peptide Synthesis", Springer-Verlag, NY (1984).
British Journal of Haematology, "Flt3 mutations and leukaemia", 2003,122(4):523-38.
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Canibano, V. et al., Synthesis 14, 2175 (2001).
ChemBlink. Tipifarnib. Electronic Resource. Retrived on Dec. 18, 2010: [http://www.chemblink.com/products/192185-72-1.htm].
Coll. Czech. Chem. Commun.: 31(11), 4432-41, (1966), Palecek, J.
Cummins et al., Tetrahedron (1988), 44(16), 5151.

(56) References Cited

OTHER PUBLICATIONS

Chou Tc, Talalay P. (1984) "Quantitative analysis of dose-effect relationships: the combined effects of multiple drugs or enzyme inhibitors." Adv Enzyme Regul. 22:27-55.

Comprehensive Organic Transformations: Larock, R.S.; Wiley and Sons Inc., USA 1999.

Cortes. Farnesyltransferase inhibitors in acute myeloid leukemia and myelodysplastic syndromes. Clinical Lymphoma, vol. 4, Suppl. 1, S30-S35, 2003.

Drexler, H. G. et al. (2004), "FLT3: receptor and ligand"; Growth Factors 22(2):71-3.

Drexler, H.G., "The Leukemia-Lymphoma Cell Line Factsbook", Academic Pres:SanDiego, CA, 2000.

Ferrara et al., "Prognostic factors and therapeutic options for relapsed or refractory acute myeloid leukemia." Haematologica. Aug. 2004, vol. 89, No. 8, Aug. 2004; pp. 998-1008.

Gilliand, G., et.al, "The roles of FLT3 in mematopoiesis and leukemia", Blood. 2002; 100:1532-42.

Gotlib, J (2005) "Farnesyltransferase inhibitor therapy in acute myelogenous leukemia." Curr. Hematol. Rep.;4(1):77-84.

Gould, P., " Salt selection for basic drugs", Ref. International J. Pharm. 1986, 33, 201-217.

Gray, M. et al., Tetrahedron Lett., 41:6237-40 (2000).

Griswold, I. J. et al., "Effects of MLN518, a Dual FLT3 and KIT inhibitor, on Normal and Malignant Hematopoiesis" Blood, Jul. 2004 [Epub ahead of print].

Haluska P., G.K. Dy, A.A. Adjei. (2002) "Farnesyl transferase inhibitors as anticancer agents." Eur J Cancer. 38(13):1685-700.

Han, J., Advances in Characterization of Pharmaceutical Hydrates, Trends in Bio/PharmaceuticalIndustry, pp. 25-29. Mar., 2006.

Hartwig, J.F., "Organopalladium Chemistry for Organic Synthesis," Wiley Interscience, NY (2002).

Hellstrom et al., "Antibodies for Drug Delivery", in Controlled Drug Delivery (2nd Ed.), Robinson et al. (eds.), pp. 623-53 (Marcel Dekker, Inc. 1987).

Hengartner, MO. (2000) "The biochemistry of apoptosis." Nature 407:770-76.

Hill et al., J. Am. Chem. Soc. (1973), 95, 1338.

Iddon. B. et al., J. Chem. Soc. Perkin Trans. 1., 1370, (1980).

Ishikubo et al (Jpn J Clin Oncol 36:494-498, 2006).

Johnson et al., Brit J Cancer, 84:1424-1431 (2001).

Lyon et al., J. Med. Chem., 29: 630-634 (1986).

Romeo et al., J. Med. Chem., 46: 2877 (2003).

Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).

Katritsky, A. et al., "para-Formylation of Nitroarenes via Vicarious Nucleophilic Substitution of Hydrogen with Tris(benzotriazol-1-yl)methane", Tetrahedron Lett., 37:347-50 (1996).

Kolder, C.R., et al, "Synthesis and Reactivity of 5-Chloro-2,4-Dihydrosypyridine", x Recl. Trav. Chim. Pays-Bas; 285 (1953).

Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.

Levis, M. et al. 2001, "A FLT3 tyrosine kinase inhibitor is selectively cytoxic to acute myeloid leukemia blasts harboring FLT3 internal tandem duplication mutations", Blood 98(3):885-7.

Levis, M. et al., "Novel FLT3 tyrosine kinase inhibitors" Expert Opin. Investing. Drugs (2003) 12 (12) 1951-1962.

Levis, M. et al., "Small Molecule FLT3 Tyrosine Kinase Inhibitors" Current Pharmaceutical Design, 2004, 10, 1183-1193.

Levis, M., et al. (2004) "In vitro studies of a FLT3 inhibitor combined with chemotherapy: sequence of administration is important to achieve synergistic cytotoxic effects." Blood. 104(4):1145-50.

Nunez G, Benedict MA, Hu Y, Inohara N. (1998) "Caspases: the proteases of the apoptotic pathway." Oncogene 17:3237-45.

O'Farrell, A.M. et al. "SU11248 is a novel FLT3 tyrosine kinase inhibitor with potent activity in vitro and in vivo" Blood, May 2003; 101:3597-3605.

Olah, G.A. et al., "Formylating Agents", Chemical Reviews, vol. 87, No. 4, 1987.

Prendergast et al., (2001) "Farnesyl Transferase Inhibtors: Mechanism and Applications" Expert Opin Investig Drugs. 10(12):2105-16).

Protecting Groups, P, Kocienski Thieme Medical Publishers, 2000.

Pure Appl. Chem., 1976, 45:13-30.

Lewis, et al. "Diacetoxypiperidinium Analogs of Acetylcholine", Junal of Medicinal Chemistry, 1973, vol. 16, No. 2 pp. 156-159.

Loader, C., et al., "Pyrrole chemistry. XXIII. The cyanation of substituted pyrroles with chlorosulfonyl isocyanate (CSI). New syntheses of pyrrole-3-carbonitriles. ", Can. J. Chem, 59, 2673 (1981).

Lovborg H, Gullbo J, Larsson R. (2005) "Screening for apoptosis-classical and emerging techniques." Anticancer Drugs 16:593-9.

Major, R., et al. "1-Alkoxy-4-phenyl-4-propionoxypiperdines and Their 3-Methyl Homologs as New Analgesics", vol. 26, pp. 1867-1847, (1961).

McKenna, H.J. et al., "Mice lacking flt3 ligand having deficient hematopoiesis affecting hematopoietic progenitor cells, dendritic cells and natural killer cells", Blood Jun. 2000;95:3489-3497.

Miyaura, N. et al., "Palladium-Catalyzed Cross-Coupling Reactions of Organoboron Compounds", Chem. Rev. 95:2457 (1995).

Modern Amination Methods: Ricci, A., Ed., Wiley-VCH: Weinheim, 2000.

Muci, et al., "Practical Palladium Catalysts for C-N. And C-O Bond Formation", Top. Curr., Chem. 219-131-209 (2001.

Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.

Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.

Nicolai, E., et al., "New Process for the Synthesis of Imidazo[4-5-13] pyridine Derivatives as Potent Orally Active Thromboxane $A_2$ Receptor Antagonists", J. Heterocyclic Chemistry, 31, (73) (1994).

Quentmeier H, et al. FLT3 mutations in acute myeloid leukemia cell lines. Leukemia. Jan. 2003;17:120-124.

Sadick, M. et al., Analysis of Heregulin-Induced ErbB2 Phosphorylation with a High-Throughput Kinase Receptor Activation Enzyme-Linked Immunosorbent Assay, Analytical Biochemistry. 1996; 235:207-214.

Scheijen, B. et al. (2002), "Tyrosine kinase oncogenes innormal hematopoiesis and hematological disease", Oncogene 21(21):3314-33.

Shih L. Y. et al., (2004) "Internal tandem duplication of fms-like tyrosine kinase 3 is associated with poor outcome in patients with myelodysplastic syndrome." Cancer, 101; 989-98.

Simpson WG, The calcium channel blocker verapamil and cancer chemotherapy. Cell Calcium. Dec. 1985;6(6):449-67.

Smith, B. D. et al., "Single-agent CEP-701, a novel FLT3 inhibitor, shows biologic and clinical activity in patients with relapsed or refractory acute myeloid leukemia" Blood, May 2004; 103:3669-3676.

Smith P, "The Curtius Reaction", Organic Reactions 3:337 (1947).

Stirewalt, D.L. et al. (2003), "The role of FLT3 in haematopoietic malignancies", NatRev Cancer 3(9):650-65.

Stone, R.M. et al. "PKC 412 FLT3 inhibitor therapy in AML: results of a phase II trial" An Hematol 2004; 83 Suppl 1:S89-90.

Suzuki, A., "Metal-Catalyzed Coupling Reactions" F. Deiderich, P. Stang, Eds., Wiley-VCH, Weinheim (1998).

Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.

Thalhammer et al. Duration of second complete remission in patients with acute myeloid leukemia treated with chemotherapy: a retrospective single-center study. Ann. Hematology, 1996, 72: 216-222.

Thompson et al., Journal of Industrial and Engineering Chemistry (Washington, D. C.) (1952), 44,1659-62.

(56) References Cited

OTHER PUBLICATIONS

Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tse, K.F. et al., "Inhibition of FLT3-mediated transformation by use of a tyrosine kinase inhibitor" Leukemia, Jul. 15, 2001(7):1001-10.
van Engeland M., L.J. Nieland ,et al. (1998) "Annexin V-affinity assay: a review on an apoptosis detection system based on phosphatidylserine exposure." Cytometry. 31(1):1-9.
Walker et al (Dermatol 212:70-72, 2006; (Abstract Only).
Wustrow, et al, "Coupling of Arylboronic Acids with a Partially Reduced Pyridine Derivative" Synthesis, 993 (1991).
www.cancer.org (accessed online Mar. 2, 2010), "Can Acute Myeloid Luchemia (AML) Be Prevented?".
Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.
Beletskaya et al., *Chem. Rev.*, 100:3009 (2000).
Brase et al., *Angew. Chemie Int. Ed.*, 44(33), 5188-5240, (2005).
Brase et al., Metal-Catalyzed Cross-Coupling Reactions (2nd Edition), pp. 217-315, A. de Meijere, F. Diederich, Eds., Wiley-VCH, Weinheim (2004).
Corey et al., *Tetrahedron Lett.*, 29, 995 (1988).
Couturier et al., *Organic Process Research & Development*, 2002, 6, 42-48.
Dirlam et al., *J. Heterocyclic Chem*, 17, 409, (1980).
Dolan, S., et al, *J. Chem., Soc., Chem. Commun.*, 1588-9 (1985).
Fohlisch et *Liebigs Annalen der Chemie*, (1), 1-5 (1987) [English Abstract provided].
Galemmo et al., *J. Med. Chem.*, 33(10), 2828-41; (1990).
Guanti et al., *Tetrahedron*, 46 (20), 7081, (1990).
Guanti et al., *Tetrahedron: Asymmetry* 8(13), 2175-2187, (1997).
Hayakawa et al., *Bioorg. Med. Chem. Lett.*, 14(2): 455-8 (2004).
Itsuno et al., Synthesis, 12, 995-6, (1988).
Koutek, et al, Synth. Commun., 6 (4), 305-8 (1976).
Leonard et al., *J. Org. Chem.*, 28, 3021, (1963).
Liu et al., J. Am. Chem. Soc. 2004, 126, 5182.
Martinez_Teipel et al., QSAR & Combinatorial Science, 23(10), 854-858 (2004).
Mock et al., J. Phys. Org. Chem., 16(3), 175-182 (2003).

Myles et al., J. Org. Chem., 55, 1636 (1990).
Nguyen et al., Tetrahedron, 62(4), 647-651; (2006).
Nose et al., Chem. Pharm. Bull., 38(8), 2097-101, (1990).
Quintard et al., J. Org. Chem., 48: 1559-60 (1983).
Reed et al., Synthetic Communications, 20(4), 563-71, (1990).
Roush, W., J. Am. Chem. Soc. 102, 1390 (1980).
Tohma et al., Adv. Syn. Catalysis, 346, 111-124 (2004).
Wustrow et al., Tetrahedron Lett., 35, 61-4 (1994).
Suzuki, A. *In Metal-Catalyzed Cross Coupling Reactions*; Diederich, F., Stang, P. J., Eds.; Wiley-VCH: Weinheim, Germany, 1998; Chapter 2, pp. 49-89.
Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.
McOmie, J. F. W., "Protecting Groups in Organic Chemistry", 1973.
Albaneze-Walker, J., et al., "Improved Carbonylation of Heterocyclic Chlorides and Electronically Challenging Aryl Bromides", Organic Letters, vol. 6, No. 13, pp. 2097-2100 (2004).
Barnard, C., "Carabonylation of Aryl Halides Extending the Scope of the Reaction", Organic Process Research & Development, vol. 12, pp. 566-574 (2008).
Wall, M., et al., "Cyano-Substituted 2-Carboxylimidazoles: Synthesis of 4-Cyano-1-{{2- tri-methylsily]methyl}-1H-imiddazole-2-carboxylate Potassium Salt", Synthesis, No. 21, pp. 3377-3379 (2008).
Magnus, P., et al., "Synthesis osf the ABCD-rings of the Insecticidal Indole Alkaloid Nodulisporic Acid", Tetrahedron Letters, vol. 40, pp. 6909-6912 (1999).
Vippagunta, et al., "Crystalline Solids", vol. 48, Advanced Drug Delivery Review, pp. 3-26 (2001).
Wilson, et al., "Reducing Ion Channel Activity in a Series of 4-Heterocyclic Arylamide FMS Inhibitors", Bioorganic & Medicinal Chemical Letters, pp. 3925-3929 (2010).
International Search Report for corresponding Patent Application No. PCT/US2008/080081 dated Mar. 19, 2009.
International Search Report for corresponding Patent Application No. PCT/US2005/037868 dated Sep. 17,2008.
U.S. Appl. No. 07/0249680, filed Oct. 25, 2007 (Illig C., et al.).
U.S. Appl. No. 06/148,812, filed Jul. 6, 2006 (Illig, C., et al.).
Brennfuhrer, et al., "Palladium-Catalyzed Carbonylation Reactions of Aryl Halides and Related Compounds", Angewandte Chemie. International Edition, Wiley VCH Verlag, Weinheim, (2009), vol. 48, No. 23, pp. 4114-4133.
International Search Report for corresponding Patent Application No. PCT/US2013/053602 mailed Oct. 21, 2013.

PROCESS FOR THE PREPARATION OF C-FMS KINASE INHIBITORS

RELATED APPLICATIONS

This application claims the benefit of U.S. Provisional Patent Application No. 61/680,446, filed Aug. 7, 2012, which is hereby incorporated by reference in its entirety.

FIELD OF THE INVENTION

The present invention is directed to a process for the preparation of heterocyclic derivatives useful as protein tyrosine kinase inhibitors, more particularly inhibitors of c-fms kinase.

BACKGROUND OF THE INVENTION

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The over-expression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors.

Illig, C., et al., in US Patent Publication US2009/0105296 A1, published Apr. 23, 2009 discloses c-fms kinase inhibitors of the following structural formula

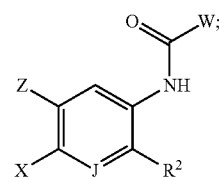

and pharmaceutically acceptable salts thereof; and a process for their preparation. Illig, C., et al., in Scheme 1, teach preparation of the derivatives of the above structural formula comprising reacting a compound of formula 1-5

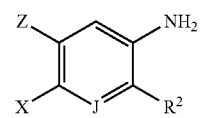

with a heterocyclic acid $P^1$—WCOOH (or a corresponding salt thereof $P^1$—WCOOM$^2$, where M$^2$ is Li, Na or K) where $P^1$ is an optional protecting group (for example 2-(trimethylsilyl)ethoxymethyl (SEM) such as when W is imidazole, triazole, pyrrole, or benzimidazole). The coupling can be carried out according to standard procedures for amide bond formation or by reaction with acid chlorides $P^1$—WCOCl or activated esters $P^1$—WCO$_2$R$^q$ (where R$^q$ is a leaving group such as pentafluorophenyl or N-succinimide).

There remains a need for a process for the preparation of compounds of formula (I), wherein the said process is suitable for large scale manufacture.

SUMMARY OF THE INVENTION

The present invention is directed to a process for the preparation of compounds of formula (XII)

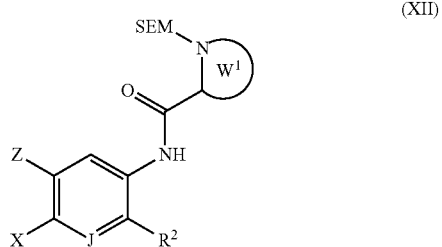

wherein

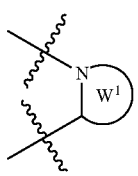 [SMILES: *CN*]

is selected from the group consisting of

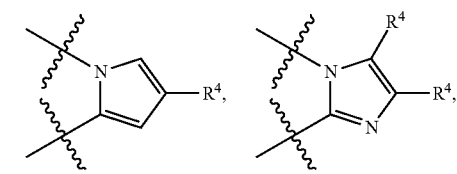

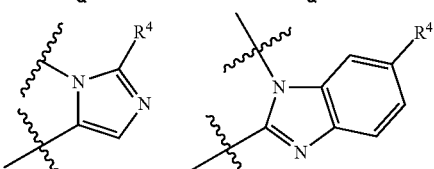

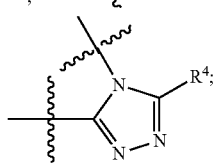

each $R^4$ is independently selected from the group consisting of hydrogen, F, Cl, Br, I, —OH, —OCH$_3$, —OCH$_2$CH$_3$, —SC$_{(1-4)}$alkyl, —SOC$_{(1-4)}$alkyl, —SO$_2$C$_{(1-4)}$alkyl, —C$_{(1-3)}$alkyl, —CO$_2$R$^d$, —CONR$_e$R$^f$, —CCR$^g$ and —CN;

wherein $R^d$ is selected from the group consisting of H and —C$_{(1-3)}$alkyl; $R^e$ is selected from the group consisting of H and —C$_{(1-3)}$alkyl; $R^f$ is selected from the group consisting of H and —C$_{(1-3)}$alkyl; and $R^g$ is selected from the group consisting of hydrogen, —CH$_2$OH and —CH$_2$CH$_2$OH;

J is selected from the group consisting of CH and N;

$R^2$ is selected from the group consisting of cycloalkyl, spiro-substituted cycloalkenyl, thiophenyl, dihydrosulfonopyranyl, phenyl, furanyl, tetrahydropyridyl and dihydropyranyl; any of which may be independently substituted with one or two of each of the following: chloro, fluoro, hydroxy, and C$_{(1-4)}$alkyl;

Z is selected from the group consisting of hydrogen, F, Cl and CH$_3$;

X is selected from the group consisting of

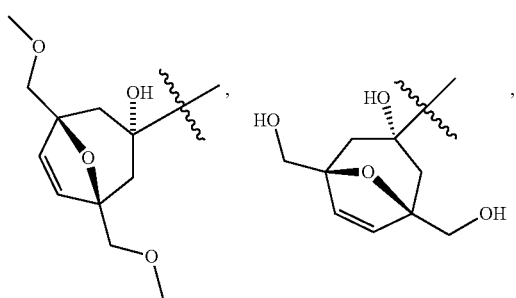

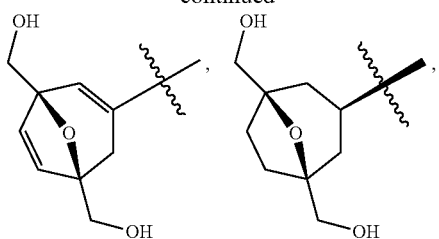

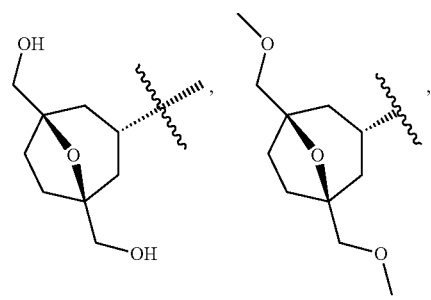

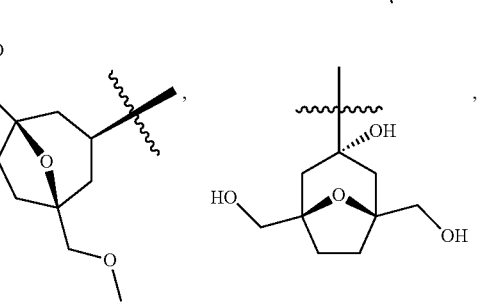

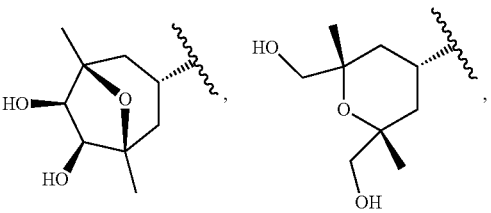

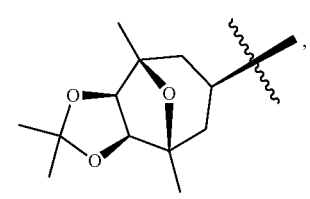

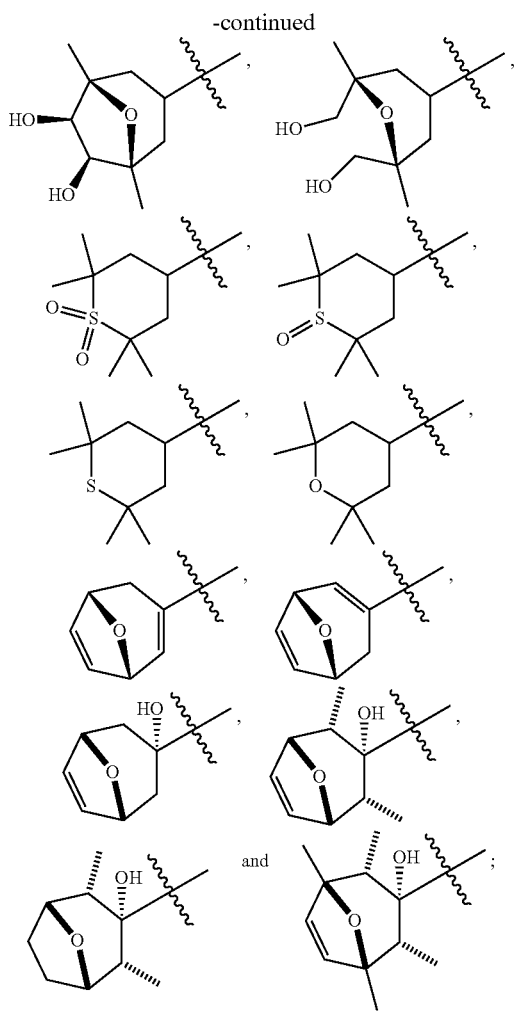

wherein $R^w$ is selected from the group consisting of hydrogen, —$C_{(1-4)}$alkyl, —$CO_2C_{(1-4)}$alkyl, —$CONH_2$, —$CONHC_{(1-4)}$alkyl, —$CON(C_{(1-4)}$alkyl$)_2$ and $COC_{(1-4)}$alkyl.

or a tautomer or pharmaceutically acceptable salt thereof; comprising

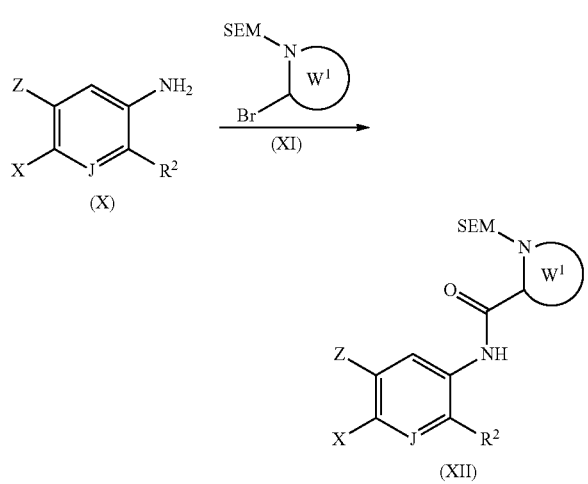

reacting a compound of formula (X) with a compound of formula (XI) or mixture of SEM protected regioisomers thereof; in the presence of carbon monoxide gas or a source of carbon monoxide; in the presence of an organic or inorganic base; in the presence of a suitably selected coupling system comprising a palladium compound and a ligand; in an organic solvent; at a temperature in the range of from about 60° C. to about 120° C. to yield the corresponding compound of formula (XII).

The present invention is further directed to a process for the preparation of compounds of formula (I)

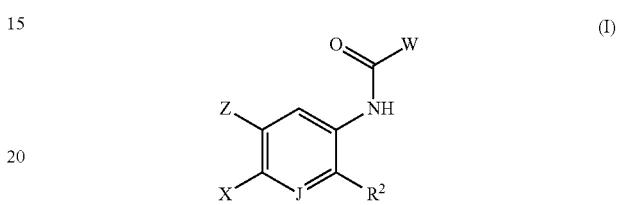

wherein

W is selected from the group consisting of

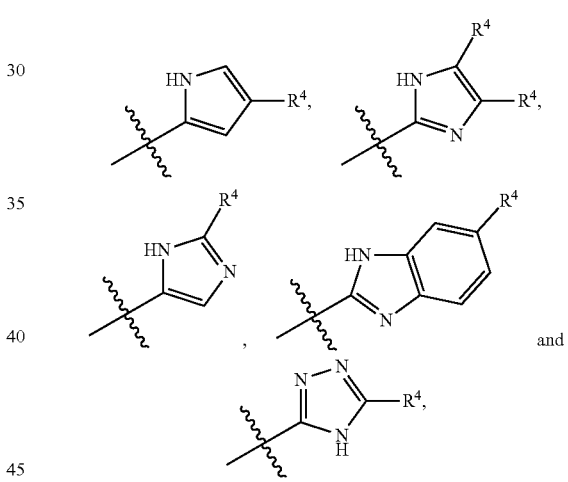

each $R^4$ is independently selected from the group consisting of hydrogen, F, Cl, Br, I, —OH, —$OCH_3$, —$OCH_2CH_3$, —$SC_{(1-4)}$alkyl, —$SOC_{(1-4)}$alkyl, —$SO_2C_{(1-4)}$alkyl, —$C_{(1-3)}$alkyl, —$CO_2R^d$, —$CONR^eR^f$, —$CCR^g$ and —CN;

wherein $R^d$ is selected from the group consisting of H and —$C_{(1-3)}$alkyl; $R^e$ is selected from the group consisting of H and —$C_{(1-3)}$alkyl; $R^f$ is selected from the group consisting of H and —$C_{(1-3)}$alkyl; and $R^g$ is selected from the group consisting of hydrogen, —$CH_2OH$ and —$CH_2CH_2OH$;

J is selected from the group consisting of CH and N;

$R^2$ is selected from the group consisting of cycloalkyl, spiro-substituted cycloalkenyl, thiophenyl, dihydrosulfonopyranyl, phenyl, furanyl, tetrahydropyridyl and dihydropyranyl; any of which may be independently substituted with one or two of each of the following: chloro, fluoro, hydroxy, and $C_{(1-4)}$alkyl;

Z is selected from the group consisting of hydrogen, F, Cl and $CH_3$;

X is selected from the group consisting of
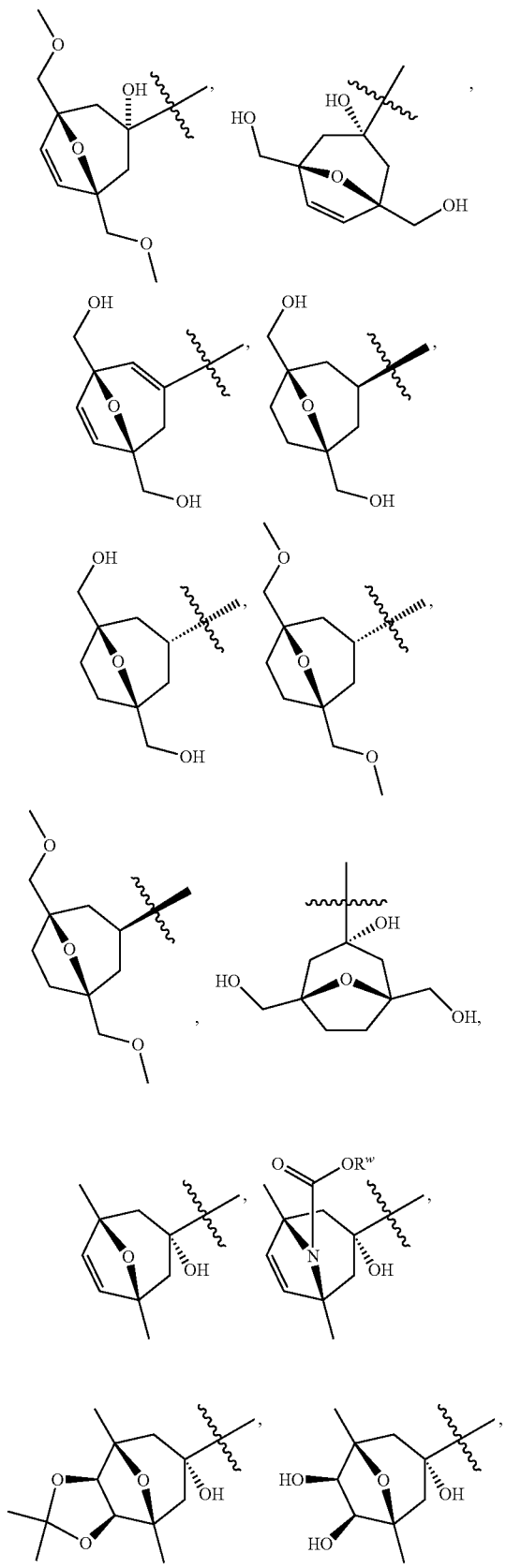
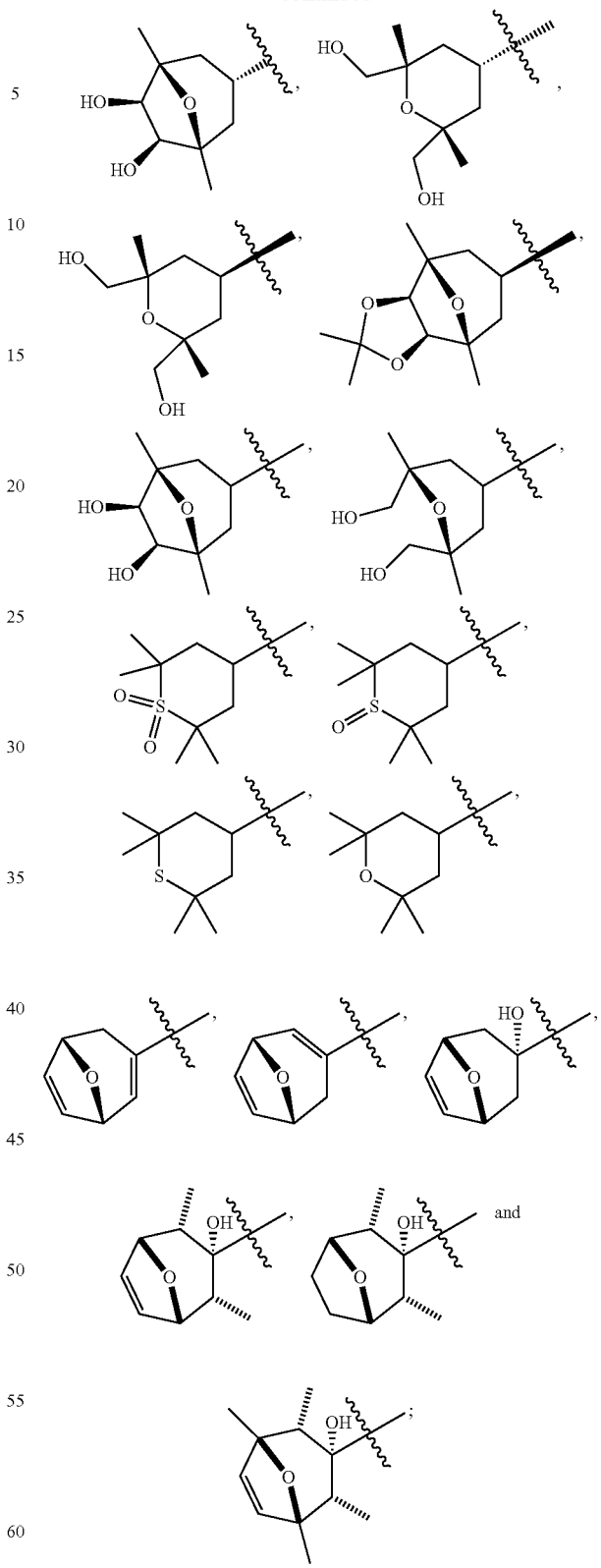
wherein $R^w$ is selected from the group consisting of hydrogen, $-C_{(1-4)}$alkyl, $-CO_2C_{(1-4)}$alkyl, $-CONH_2$, $-CONHC_{(1-4)}$alkyl, $-CON(C_{(1-4)}$alkyl$)_2$ and $-COC_{(1-4)}$alkyl.

or a tautomer or pharmaceutically acceptable salt thereof; comprising

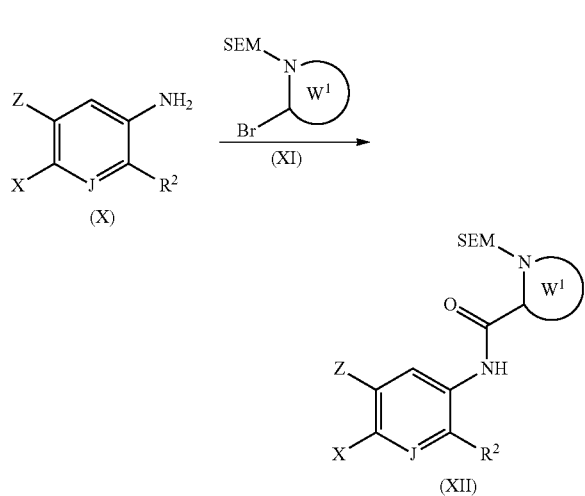

reacting a compound of formula (X) with a compound of formula (XI) or mixture of SEM protected regioisomers thereof; wherein

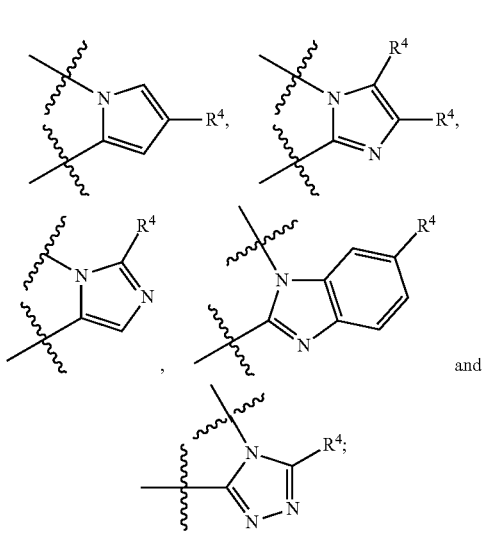

is selected from the group consisting of in the presence of carbon monoxide gas or a source of carbon monoxide; in the presence of an organic or inorganic base; in the presence of a suitably selected coupling system comprising a palladium compound and a ligand; in an organic solvent; at a temperature in the range of from about 60° C. to about 120° C. to yield the corresponding compound of formula (XII);

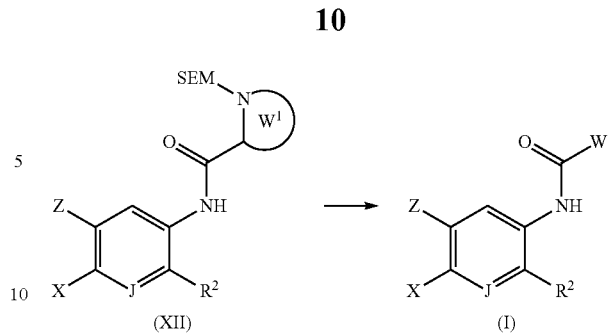

de-protecting the compound of formula (XII), to yield the corresponding compound of formula (I).

In an embodiment, the present invention is directed to a process for the preparation of a compound of formula (XII-S)

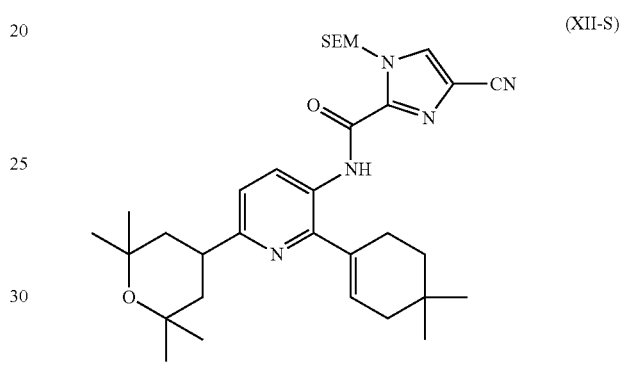

or a tautomer or pharmaceutically acceptable salt thereof; comprising

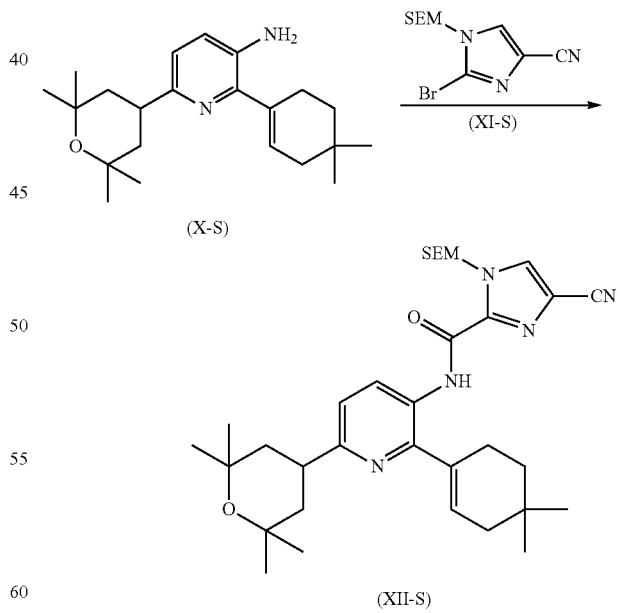

reacting a compound of formula (X-S) with a compound of formula (XI-S); in the presence of carbon monoxide gas or a source of carbon monoxide; in the presence of an organic or inorganic base; in the presence of a suitably selected coupling system comprising a palladium compound and a ligand; in an organic solvent; at a temperature in the range of from about 60° C. to about 120° C. to yield the corresponding compound of formula (XII-S).

In another embodiment, the present invention is directed to a process for the preparation of a compound of formula (I-S)

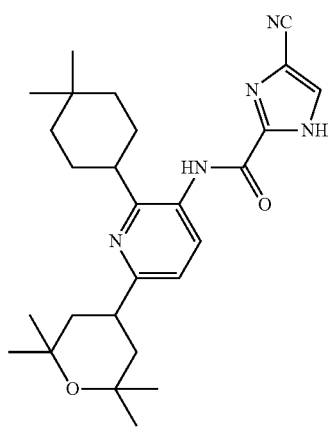

(also known 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide) or a tautomer or pharmaceutically acceptable salt thereof; comprising

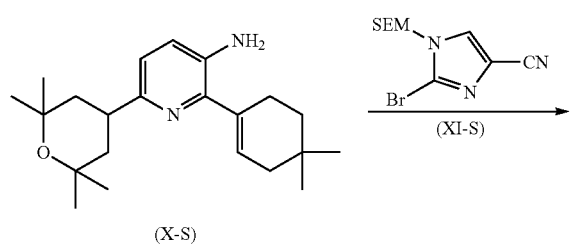

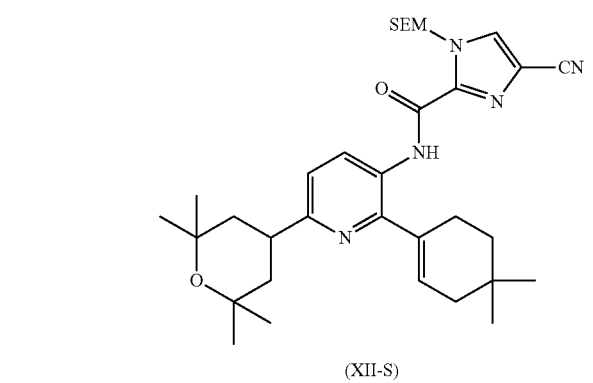

reacting a compound of formula (X-S) with a compound of formula (XI-S); in the presence of carbon monoxide gas or a source of carbon monoxide; in the presence of an organic or inorganic base; in the presence of a suitably selected coupling system comprising a palladium compound and a ligand; in an organic solvent; at a temperature in the range of from about 60° C. to about 120° C. to yield the corresponding compound of formula (XII-S)

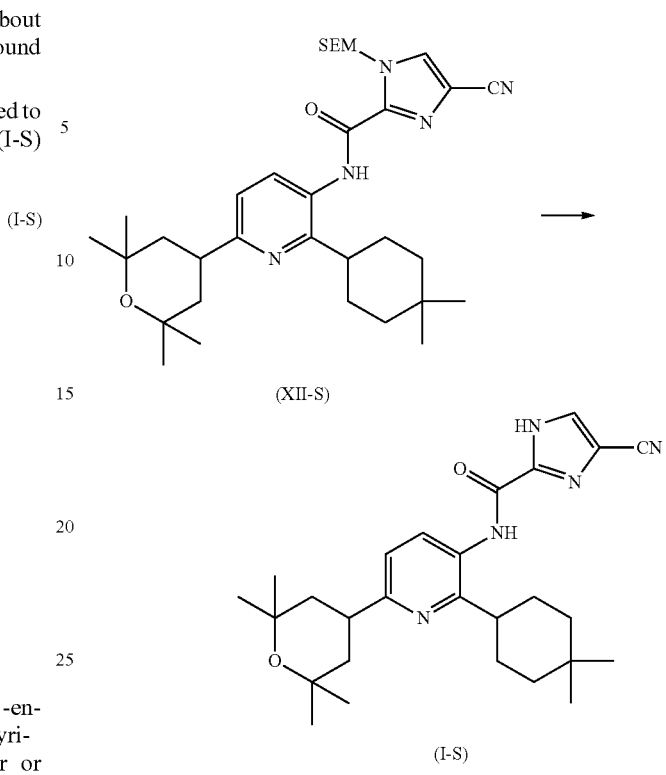

de-protecting the compound of formula (XII-S), to yield the corresponding compound of formula (I-S).

The present invention is further directed to a process for the preparation of a compound of formula (XX)

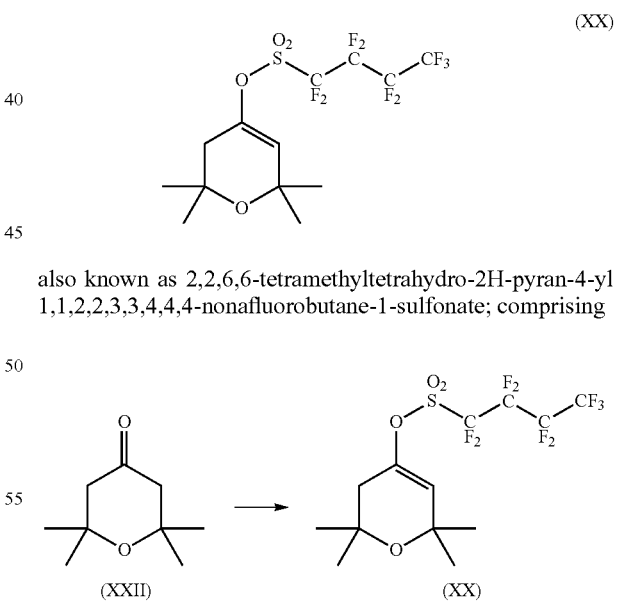

also known as 2,2,6,6-tetramethyltetrahydro-2H-pyran-4-yl 1,1,2,2,3,3,4,4,4-nonafluorobutane-1-sulfonate; comprising reacting the compound of formula (XXII) with nonafluorosulfonyl fluoride (NfsulphF); in the presence of DBU; in an organic solvent; at a temperature in the range of from about 0° C. to about room temperature; to yield the corresponding compound of formula (XX).

The present invention is further directed to a product prepared according to any of the processes described herein.

Illustrative of the invention is a pharmaceutical composition comprising a pharmaceutically acceptable carrier and a product prepared according to any of the processes described herein. An illustration of the invention is a pharmaceutical composition made by mixing a product prepared according to any of the processes described herein and a pharmaceutically acceptable carrier. Illustrating the invention is a process for making a pharmaceutical composition comprising mixing a product prepared according to any of the processed described herein and a pharmaceutically acceptable carrier.

Exemplifying the invention are methods of treating a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis; preferably rhematoid arthritis) comprising administering to a subject in need thereof a therapeutically effective amount of a compound prepared according to any of the processes described herein, or a pharmaceutical composition comprising a compound prepared according to any of the processes described herein, as described above.

In another embodiment, the present invention is directed to a product prepared according to any of the processes described herein, for use in the treatment of a disorder selected from the group consisting of osteoporosis, Paget's disease, rheumatoid arthritis other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis. Preferably, the disorder mediated by c-fms kinase is rhematoid arthritis.

In an embodiment, the present invention is directed to a product prepared according to any of the processes described herein, for use as a medicament; preferably for use as a medicament for the treatment of rheumatoid arthritis.

Another example of the invention is the use of a product prepared according to any of the processes described herein, in the preparation of a medicament for treating: (a) osteoporosis, (b) Paget's disease, (c) rheumatoid arthritis, (d) other forms of inflammatory arthritis, (e) osteoarthritis, (f) prosthesis failure, (g) osteolytic sarcoma, (h) myeloma, (i) tumor metastasis to bone, (j) ovarian cancer, (k) uterine cancer, (l) breast cancer, (m) prostate cancer, (n) lung cancer, (o) colon cancer, (p) stomach cancer, (q) hairy cell leukemia; (r) metastasis from ovarian cancer, uterine cancer, breast cancer, prostate cancer, lung cancer, colon cancer, stomach cancer, or hairy cell leukemia; (s) glomerulonephritis, (t) inflammatory bowel disease, (u) sarcoidosis, (v) congestive obstructive pulmonary disease, (w) idiopathic pulmonary fibrosis, (x) asthma, (y) pancreatitis, (z) HIV infection, (aa) psoriasis, (ab) diabetes, (ac) tumor related angiogenesis, (ad) age-related macular degeneration, (ae) diabetic retinopathy, (af) restenosis, (ag) schizophrenia, (ah) Alzheimer's dementia; (ai) pain, (aj) skeletal pain caused by tumor metastasis or osteoarthritis, or (ak) visceral pain, (al) inflammatory pain, (am) neurogenic pain; (an) an autoimmune disease, (ao) systemic lupus erythematosus, (ap) rheumatoid arthritis, (aq) other forms of inflammatory arthritis, (ar) psoriasis, (as) Sjogren's syndrome, (at) multiple sclerosis and (au) uveitis; in a subject in need thereof.

In another example, the present invention is directed to a product prepared according to any of the processes described herein, for use in a methods for treating a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis), in a subject in need thereof.

In another embodiment, the present invention is directed to a product prepared according to any of the processes described herein, for the treatment of a disorder mediated by c-fms kinase (selected from the group consisting of osteoporosis, Paget's disease, rheumatoid arthritis other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis; preferably rheumatoid arthritis).

DETAILED DESCRIPTION OF THE INVENTION

The present invention is directed to a process for the preparation of compounds of formula (XII)

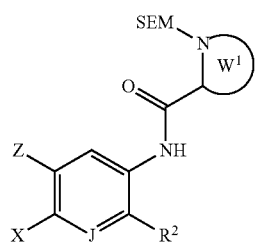
(XII)

wherein

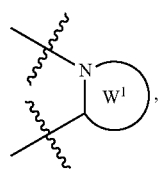 [SMILES: *CN*]

J, X, Z and $R^2$ are as herein defined. The compounds of formula (XII) are useful as intermediates in the synthesis of c-fms kinase inhibitors of formula (I). The present invention is further directed to a process for the preparation of compounds of formula (I)

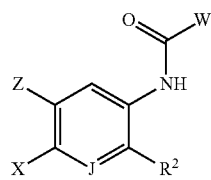
(I)

wherein W, J, X, Z and $R^2$ are as herein defined. More particularly, the process of the present invention is particularly preferred for large scale manufacture, providing cleaner reaction mixture profiles (improved product/impurity profiles) which in turn result in the elimination of additional purification step(s), increased cycle times (shorter reaction times) and reduced costs.

The compounds of formula (I) are useful as protein tyrosine kinase inhibitors, more particularly inhibitors of c-fms kinase. More particularly, as disclosed in Illig, C., et al., US Patent Publication US2009/0105296 A1, the c-fms kinase inhibitors of formula (I) are useful for the treatment of diseases including, but not limited to: osteoporosis, Paget's disease, rheumatoid arthritis, other forms of inflammatory arthritis, osteoarthritis, prosthesis failure, osteolytic sarcoma, myeloma, tumor metastasis to bone, ovarian cancer, uterine cancer, breast cancer, prostate cancer, lung cancer, colon cancer, stomach cancer, hairy cell leukemia; metastasis from ovarian cancer, uterine cancer, breast cancer, prostate cancer, lung cancer, colon cancer, stomach cancer, or hairy cell leukemia; glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia, Alzheimer's dementia; pain, skeletal pain caused by tumor metastasis or osteoarthritis, visceral pain, inflammatory pain, neurogenic pain; an autoimmune disease, systemic lupus erythematosus, rheumatoid arthritis, other forms of inflammatory arthritis, psoriasis, Sjogren's syndrome, multiple sclerosis and uveitis.

The present invention is further directed to a process for the preparation of a compound of formula (XX)

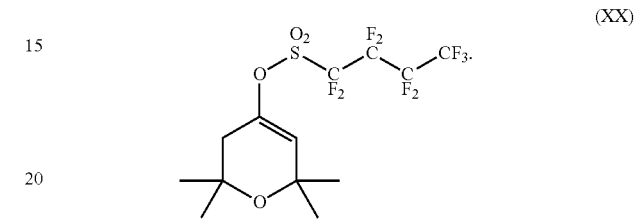
(XX)

The compound of formula (XX) is useful as an intermediate in the synthesis of compounds of formula (I), as disclosed in Illig, C., et al., U.S. Patent Publication 2009/0105296 A1.

In an embodiment, the present invention is directed to a process for the preparation of compounds of formula (I) wherein W is selected from the group consisting of

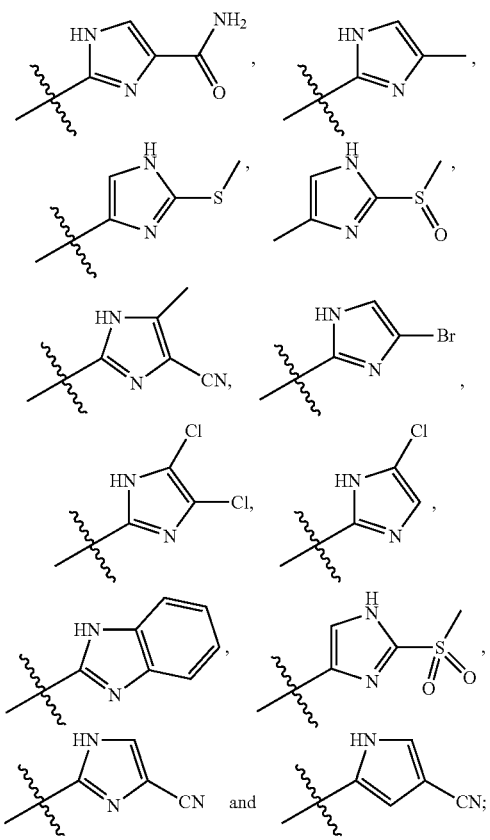

J is selected from the group consisting of CH and N;

$R^2$ is selected from the group consisting of
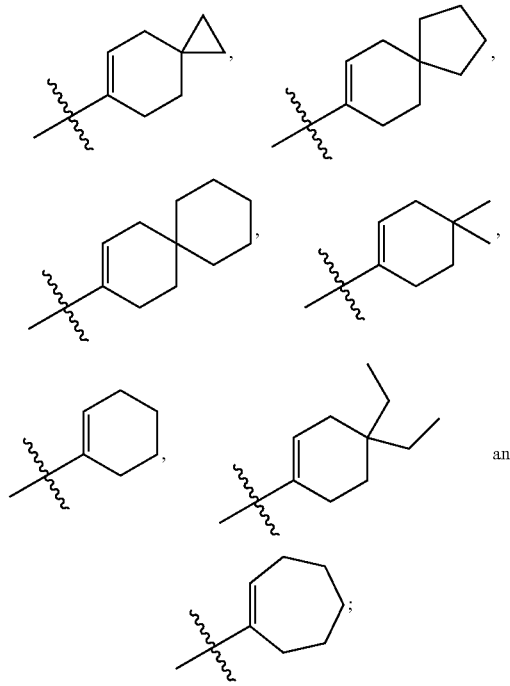
and
Z is H;
X is selected from the group consisting of
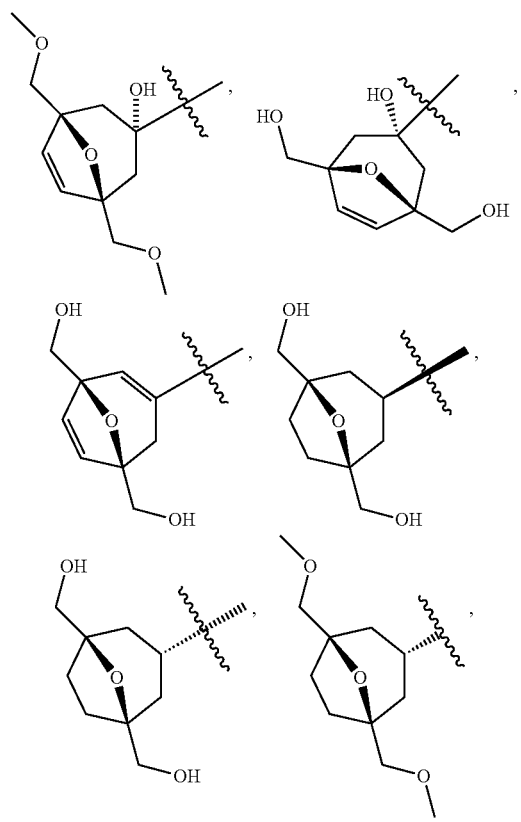
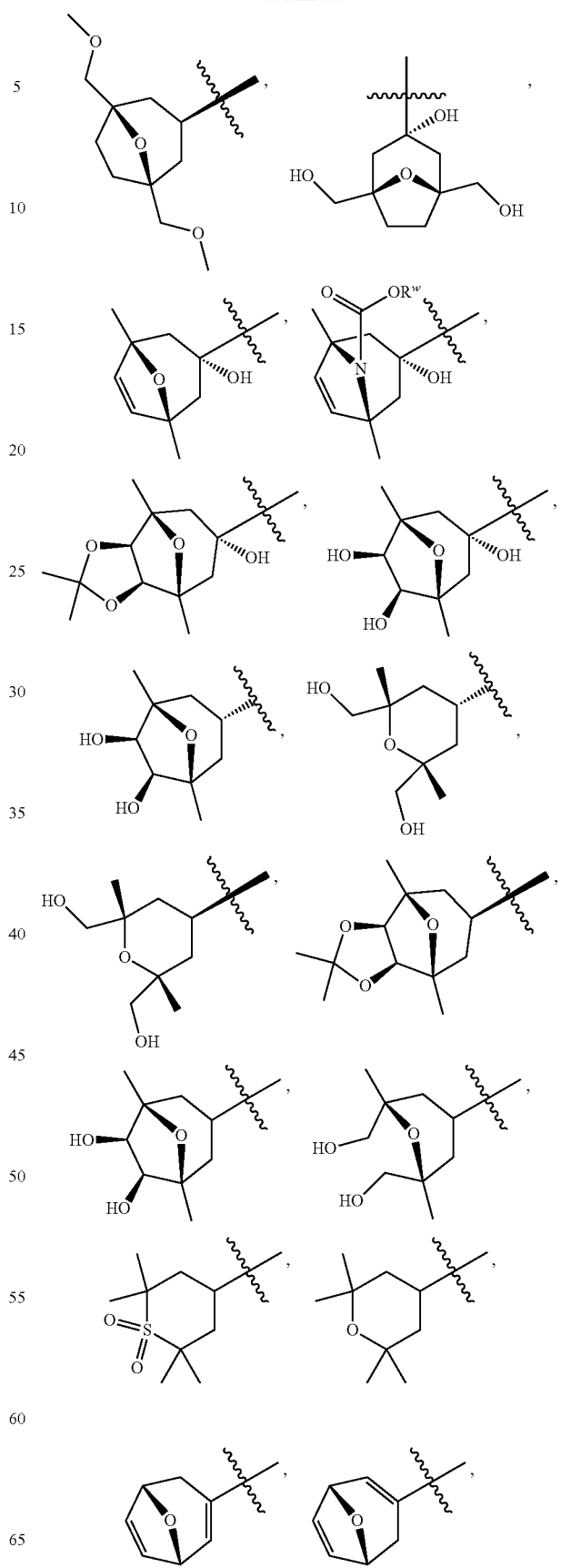

-continued

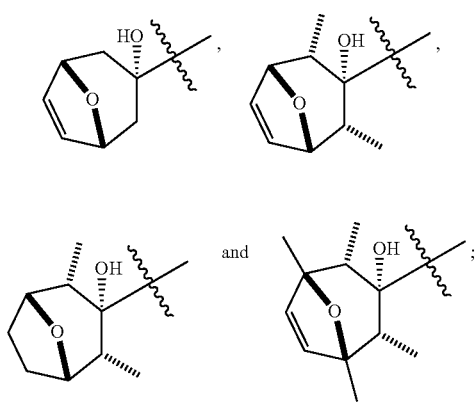

and tautomers and pharmaceutically acceptable salts thereof.

In another embodiment, the present invention is directed to a process for the preparation of compounds of formula (I) wherein W is selected from the group consisting of

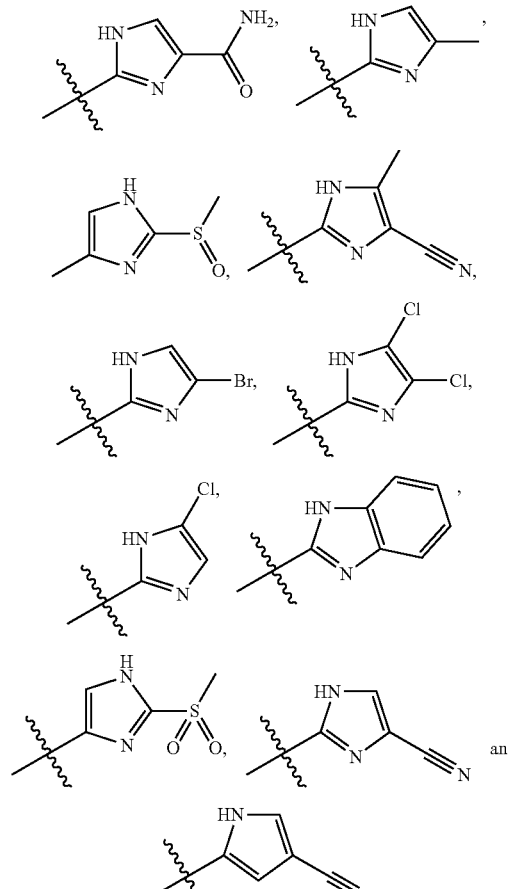

J is selected from the group consisting of CH and N;

$R^2$ is selected from the group consisting of

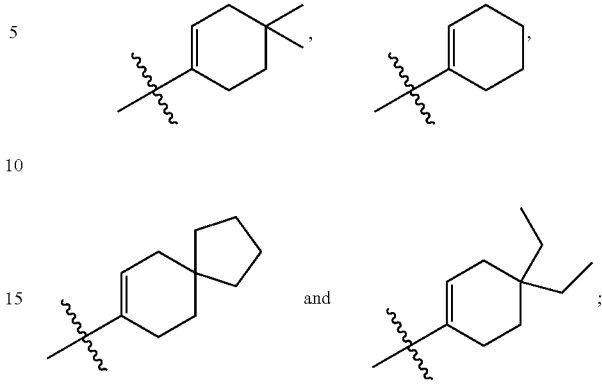

Z is H;
X is selected from the group consisting of

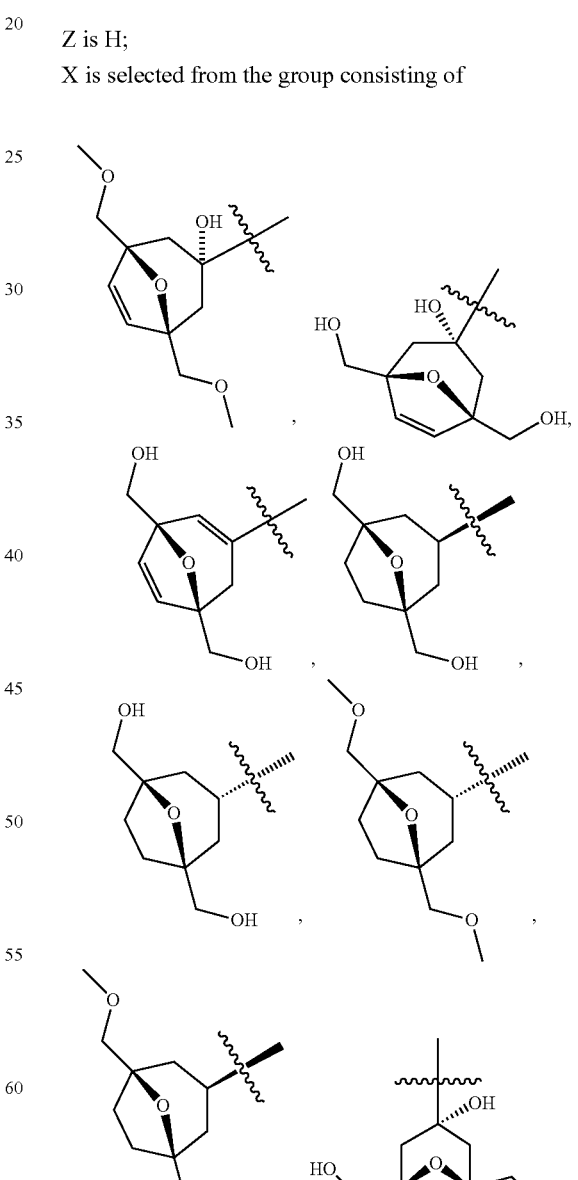

-continued

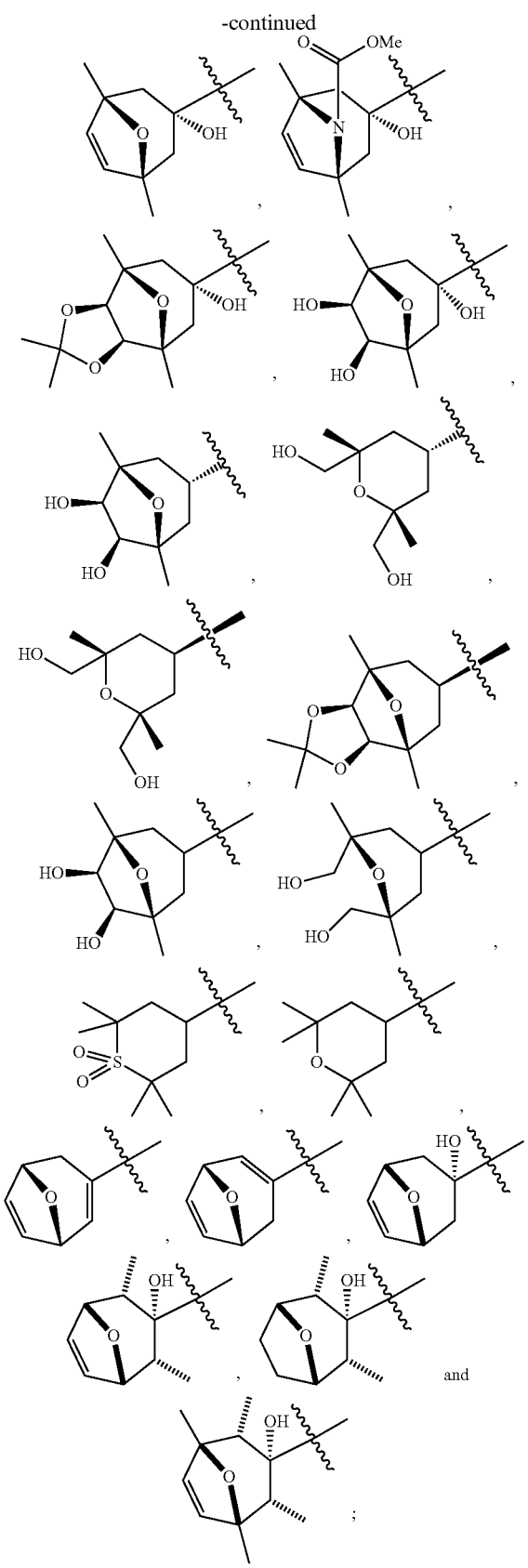

and tautomers and pharmaceutically acceptable salts thereof.

In another embodiment, the present invention is directed to a process for the preparation of compounds of formula (I) wherein W is selected from the group consisting of

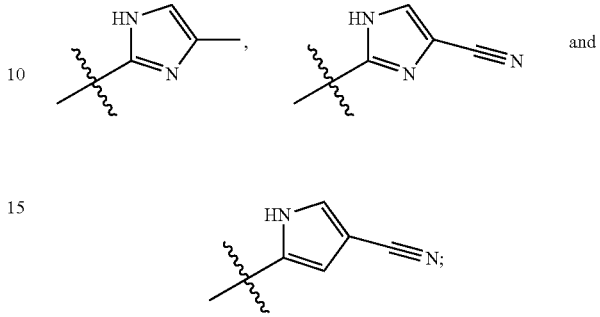

J is selected from the group consisting of CH and N;
R$^2$ is selected from the group consisting of

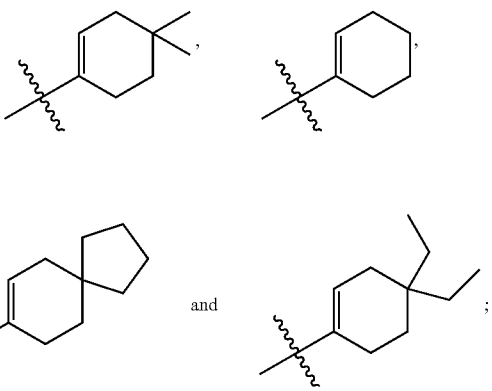

Z is H;
X is selected from the group consisting of

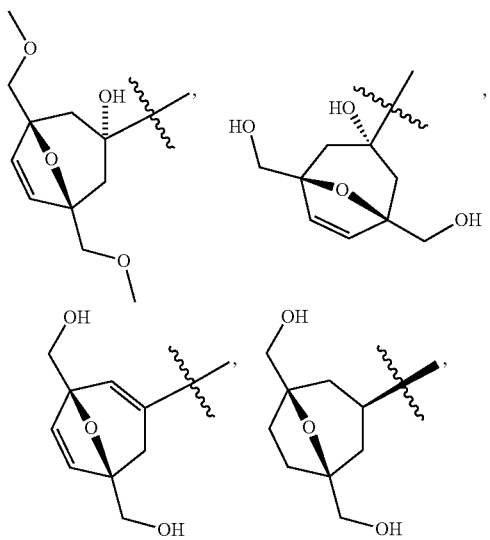

-continued
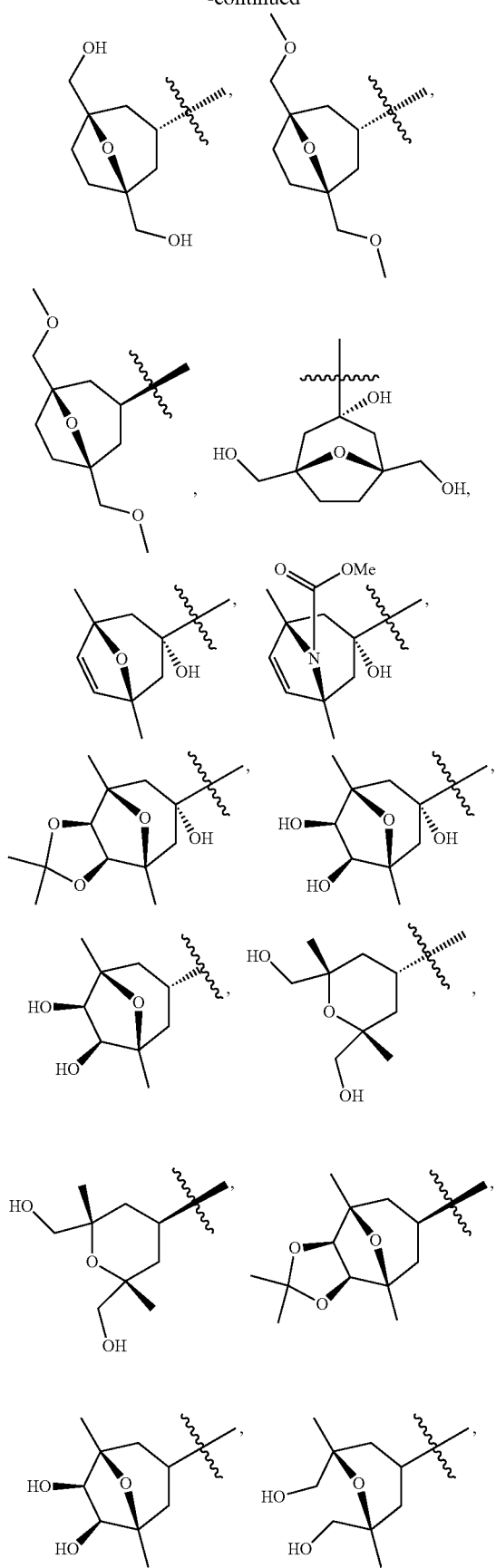
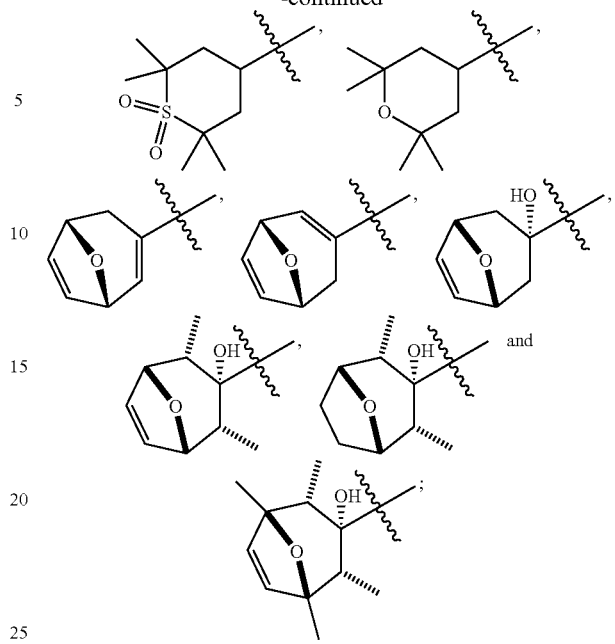
and tautomers and pharmaceutically acceptable salts thereof.
In another embodiment, the present invention is directed to a process for the preparation of compounds of formula (I) wherein
W is
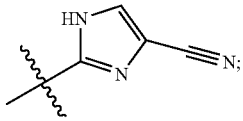 [SMILES: *c1nc(C#N)c[nH]1]
J is selected from the group consisting of CH and N;
$R^2$ is selected from the group consisting of
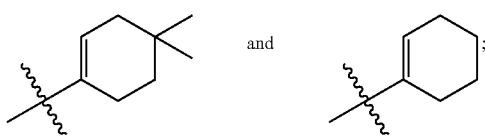
Z is H;
X is selected from the group consisting of
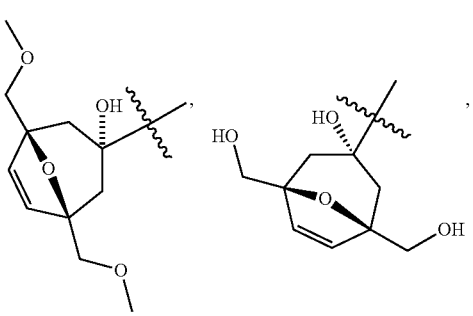

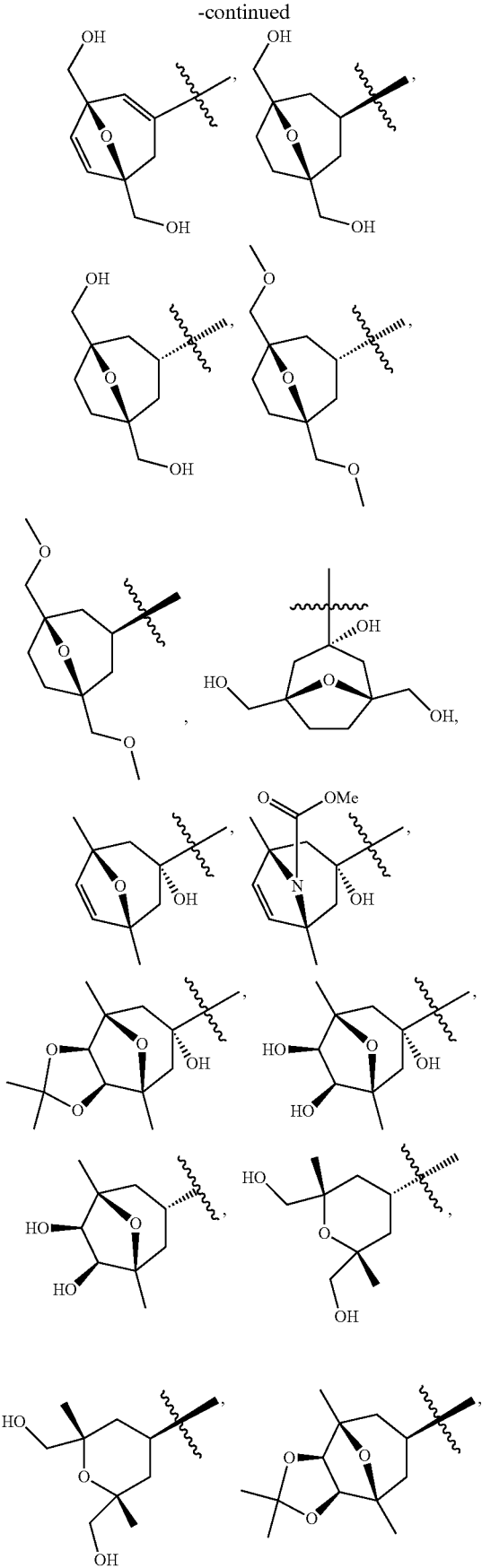
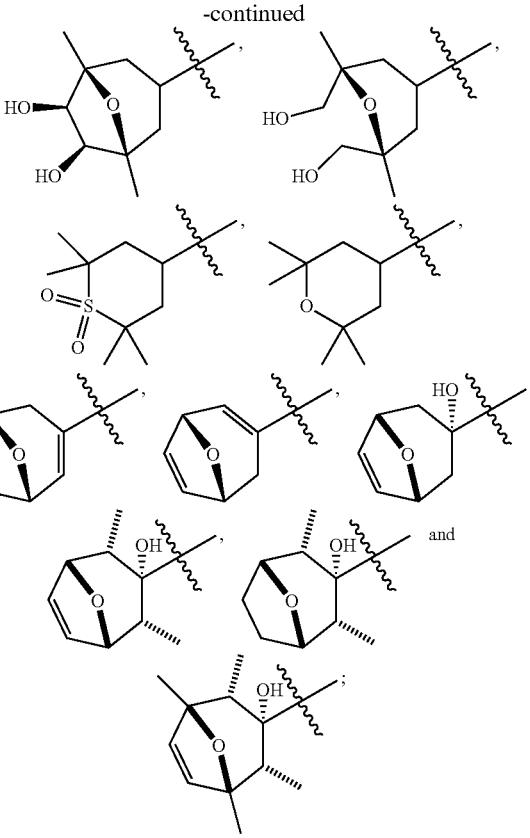
and tautomers and pharmaceutically acceptable salts thereof.
In another embodiment, the present invention is directed to a process for the preparation of compounds of formula (Ia) wherein
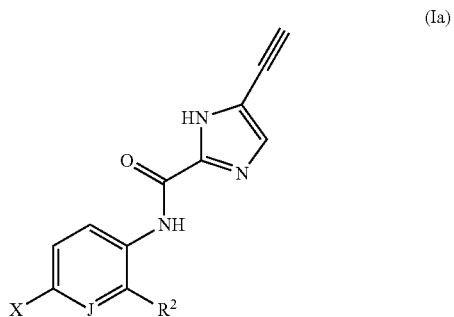
(Ia)
wherein
J is selected from the group consisting of CH and N;
R² is selected from the group consisting of
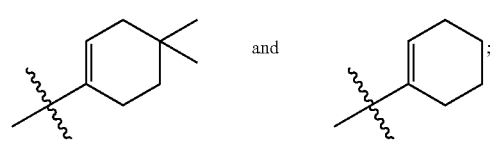
and X is selected from the group consisting of

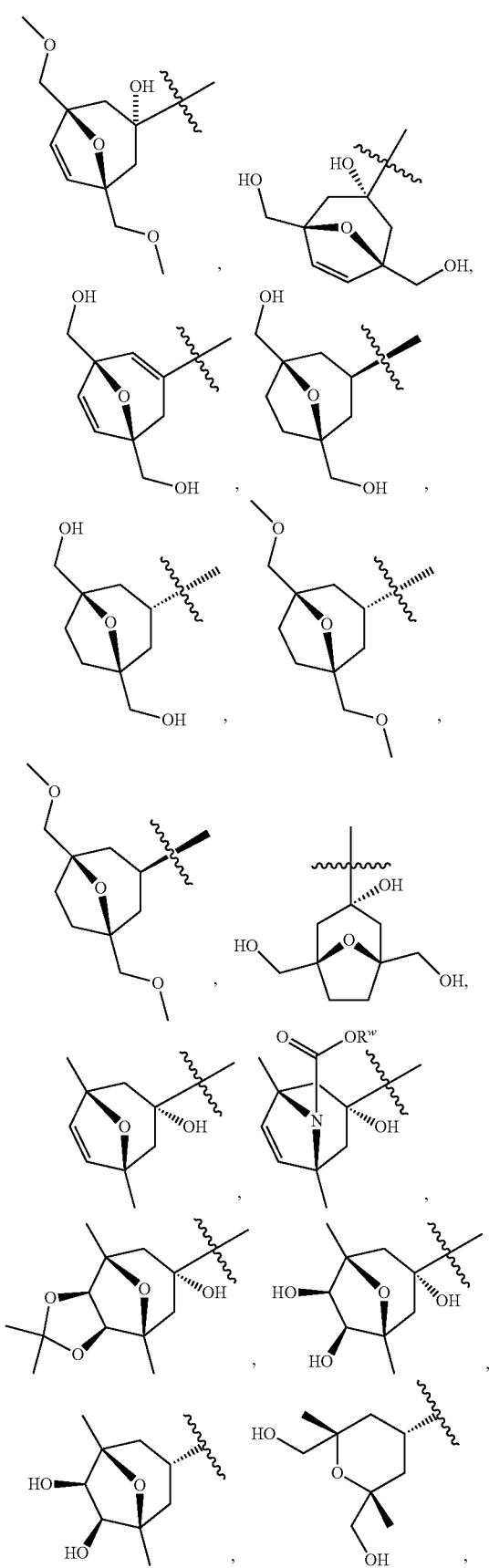

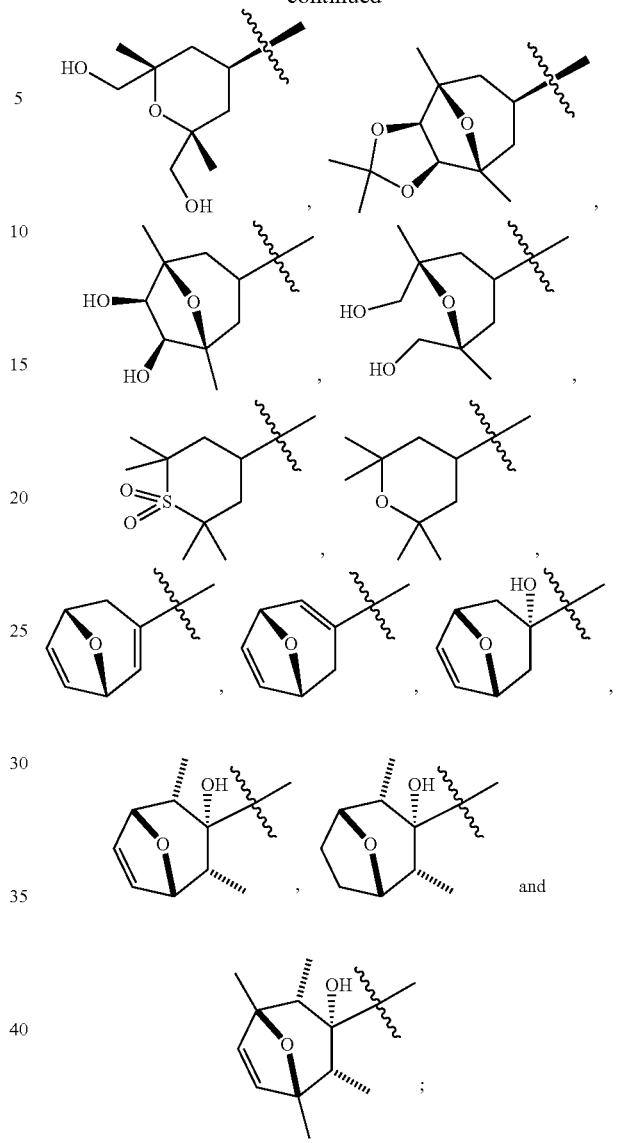

wherein $R^w$ is selected from the group consisting of hydrogen, —$C_{(1-4)}$alkyl, —$CO_2C_{(1-4)}$alkyl, —$CONH_2$, —$CONHC_{(1-4)}$alkyl, —$CON(C_{(1-4)}$alkyl$)_2$, or —$COC_{(1-4)}$alkyl;

and tautomers and pharmaceutically acceptable salts thereof.

In another embodiment, the present invention is directed to a process for the preparation of compounds of formula (Ia) wherein J is selected from the group consisting of CH and N;

$R^2$ is selected from the group consisting of

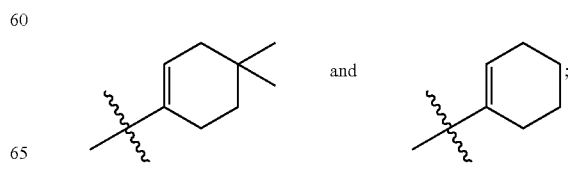

X is selected from the group consisting of
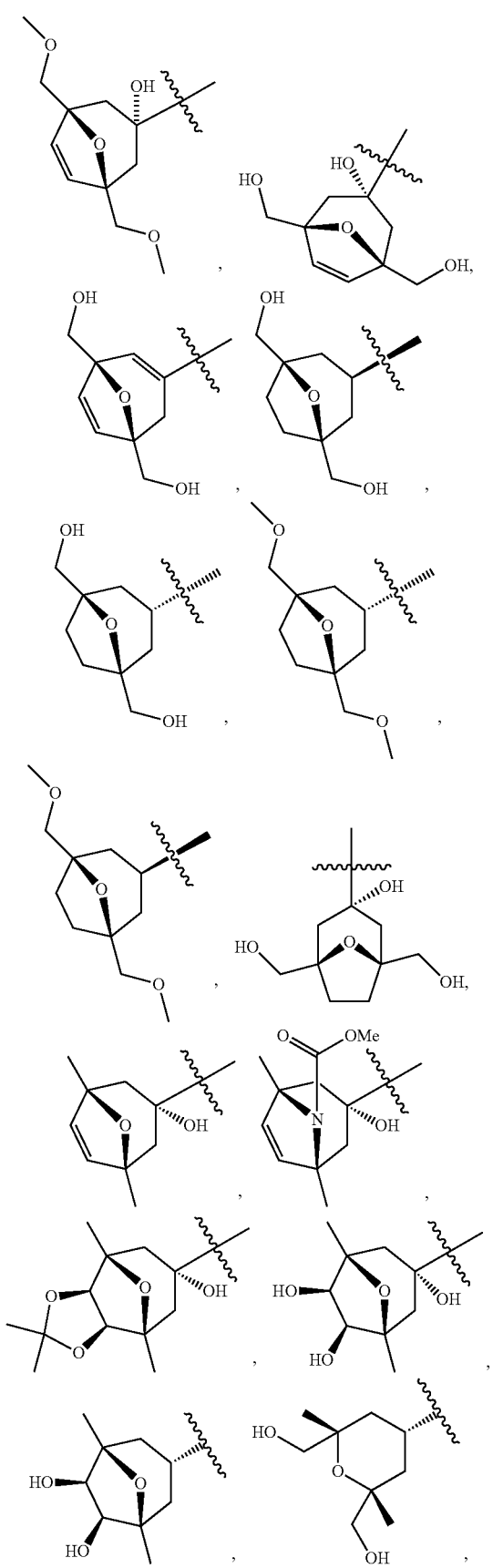
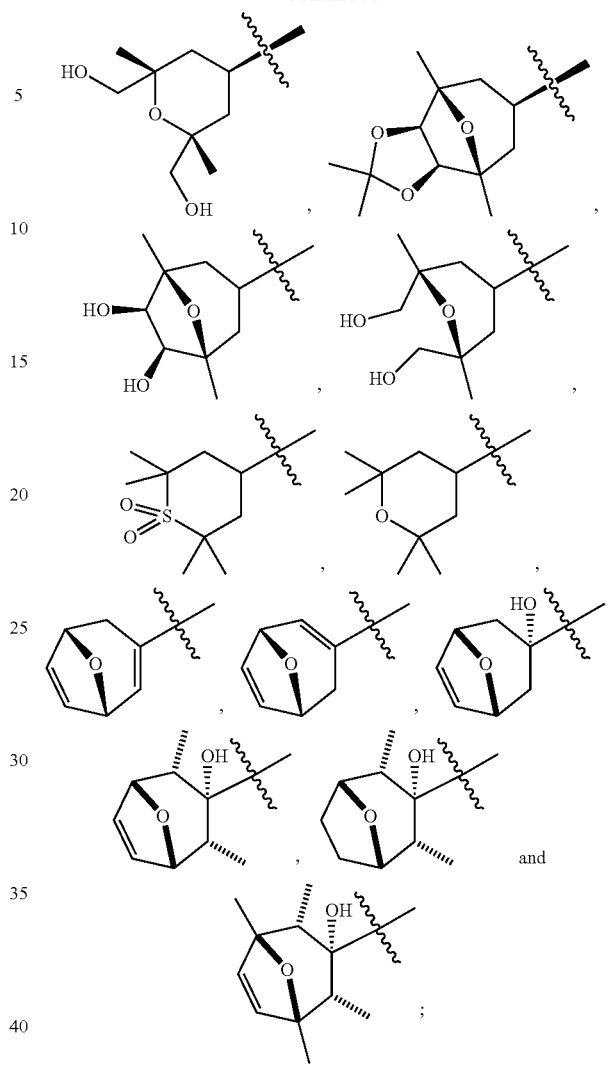
and tautomers and pharmaceutically acceptable salts thereof.
In another embodiment, the present invention is directed to a process for the preparation of compounds of formula (I) selected from the group consisting of
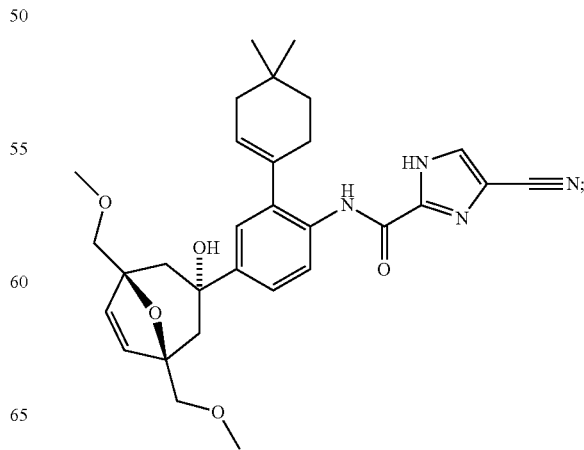

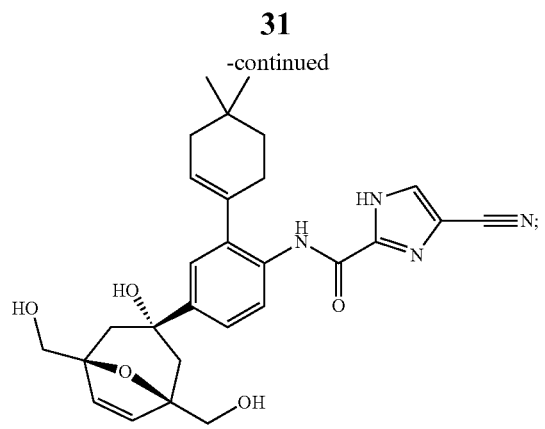
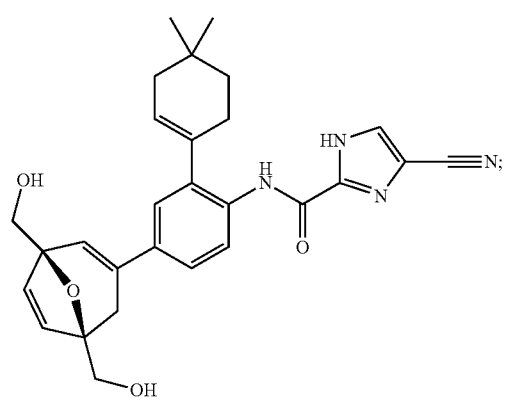
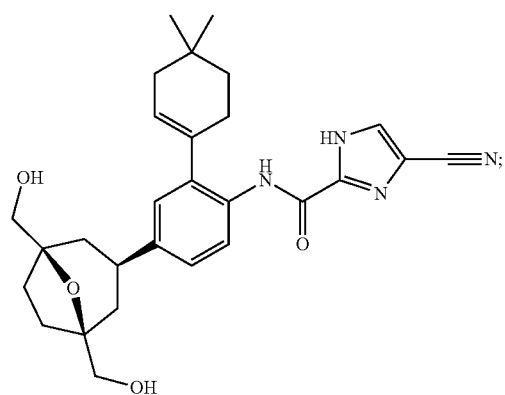
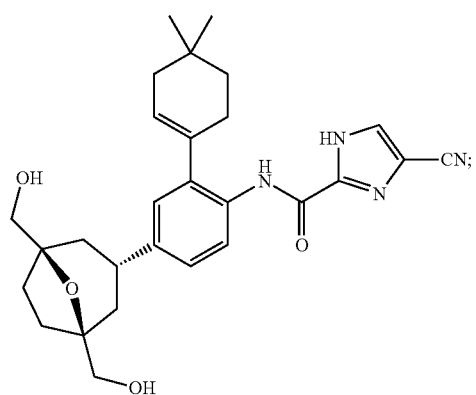
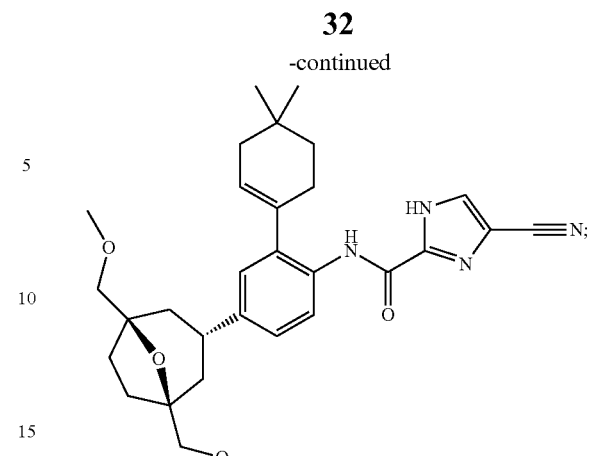
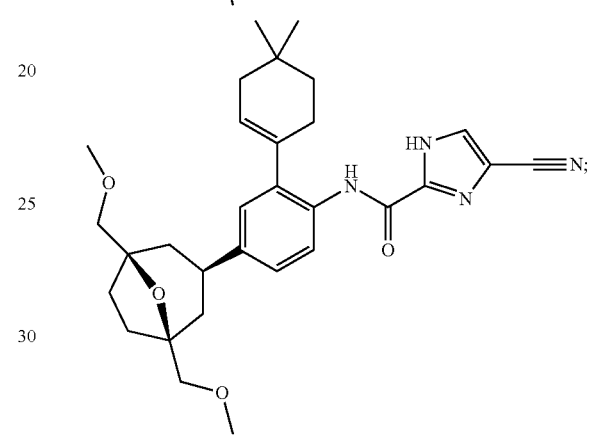
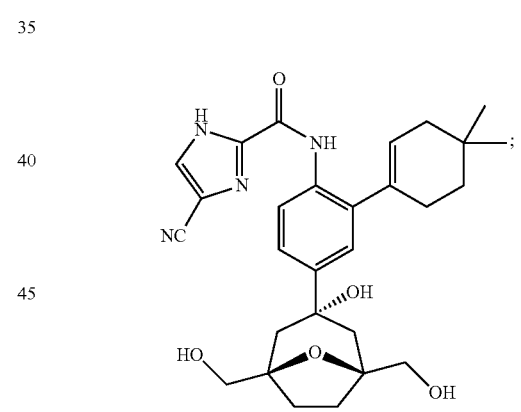
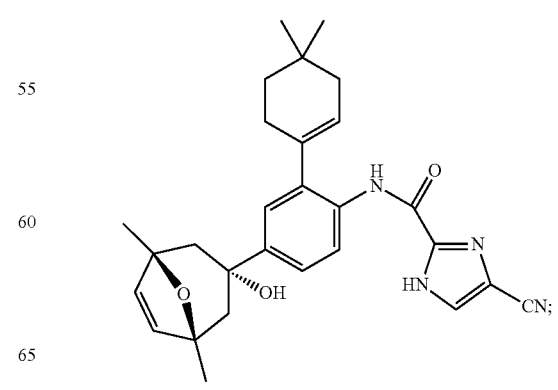

33
-continued
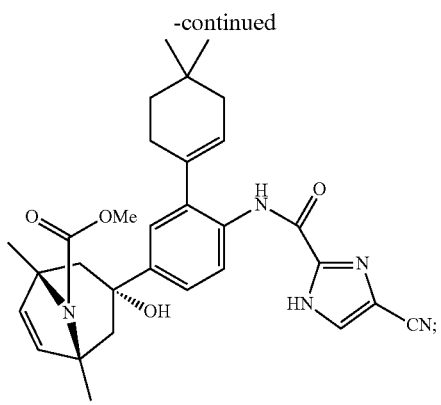
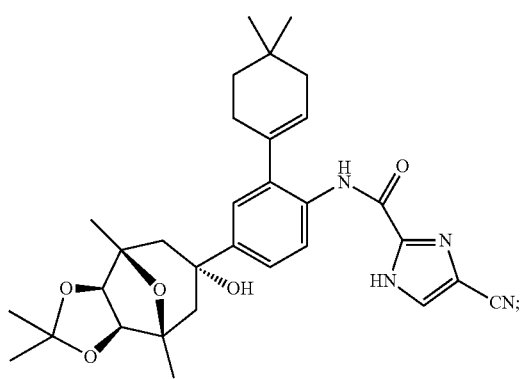
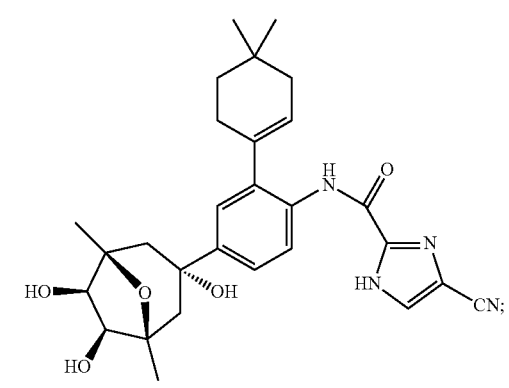
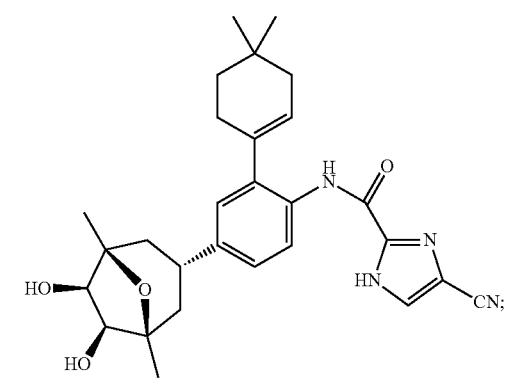
34
-continued
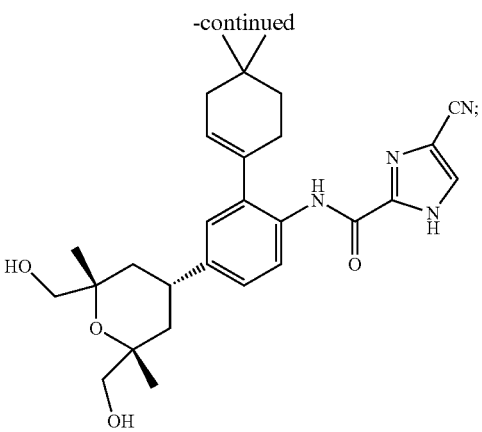
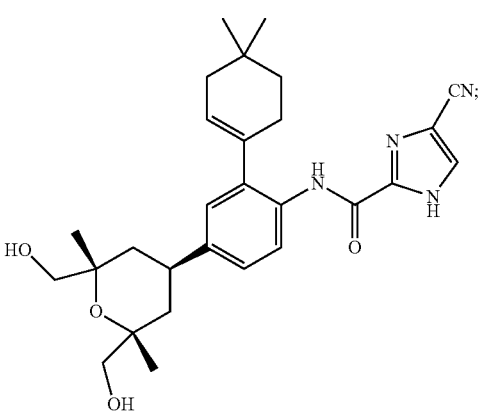
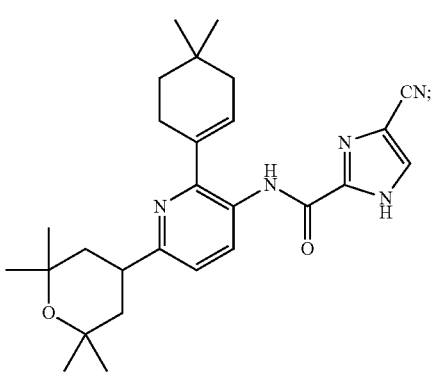
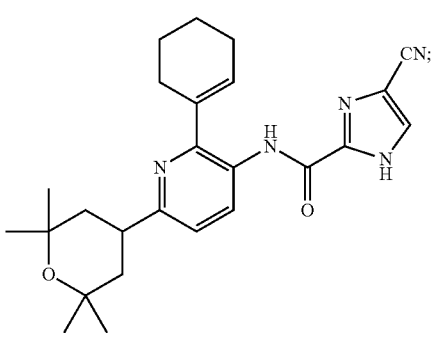

35
-continued
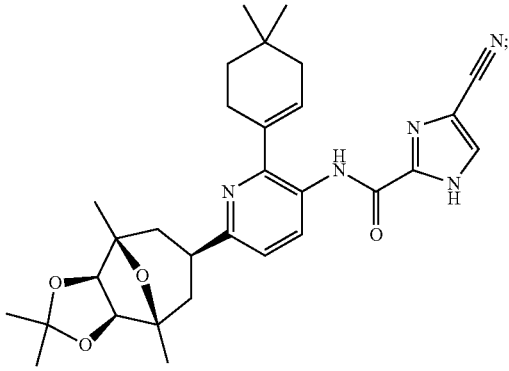
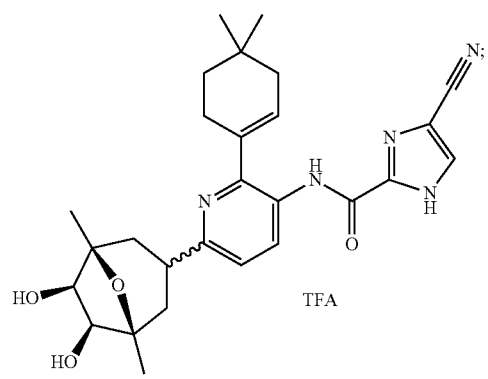
TFA
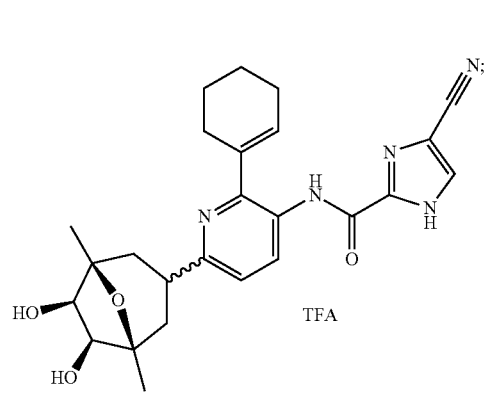
TFA
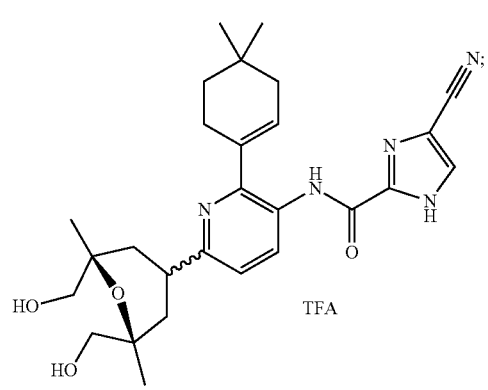
TFA
36
-continued
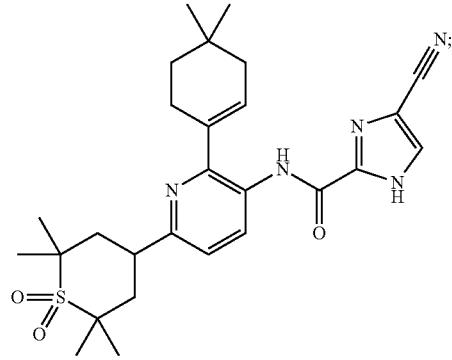
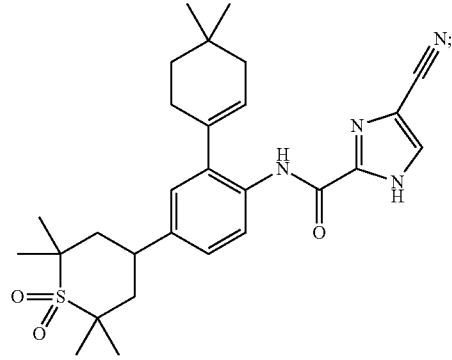
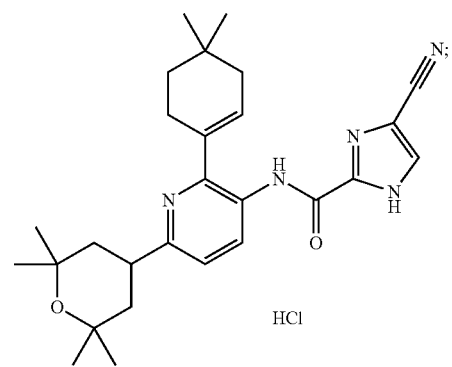
HCl
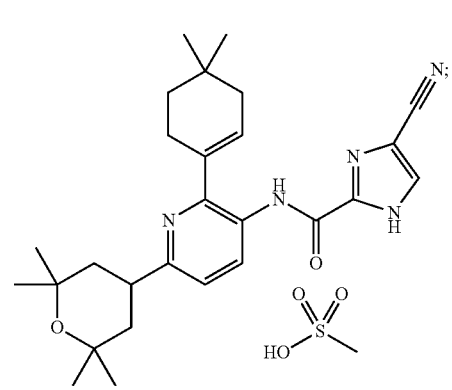

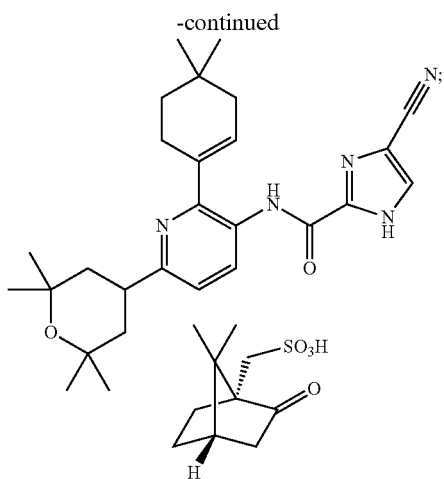

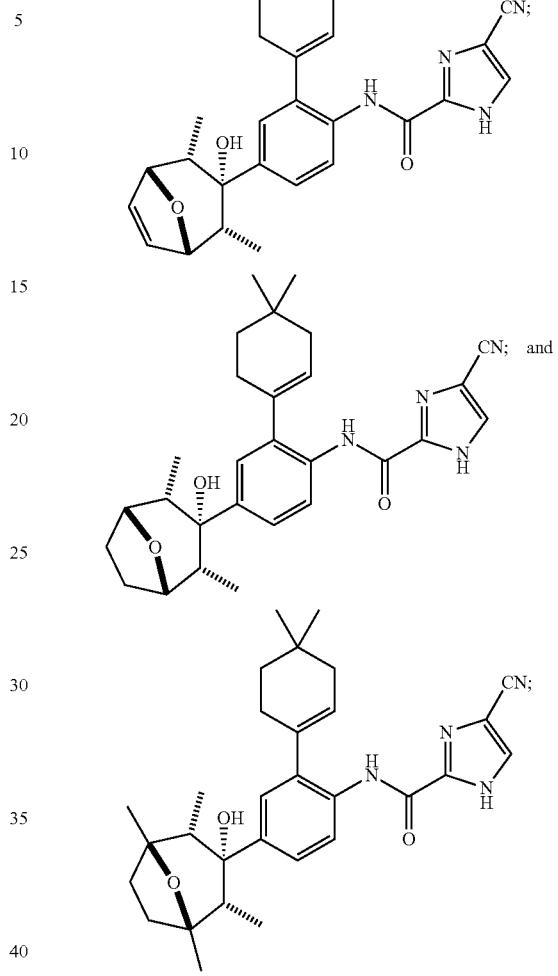

and tautomers, and pharmaceutically acceptable salts thereof.

In another embodiment, the present invention is directed to a process for the preparation of compounds of formula (I) selected from the group consisting of 4-cyano-1H-imidazole-2-carboxylic acid [2-cyclohex-1-enyl-6-(2,2,6,6-tetramethyl-tetrahydro-pyran-4-yl)-pyridin-3-yl]-amide;

4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide hydrochloride salt; 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide methanesulfonic acid salt; and 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide (1S)-(+)-10-camphorsulfonic acid salt. Most preferably, the compound is 4-cyano-1H-imidazole-2-carboxylic acid [2-(4,4-dimethyl-cyclohex-1-enyl)-6-(2,2,6,6-tetramethyl-tetrahydro-pyran-4-yl)-pyridin-3-yl]-amide hydrochloride salt.

In another embodiment, the present invention is directed to a process for the preparation of a compound of formula (I-S)

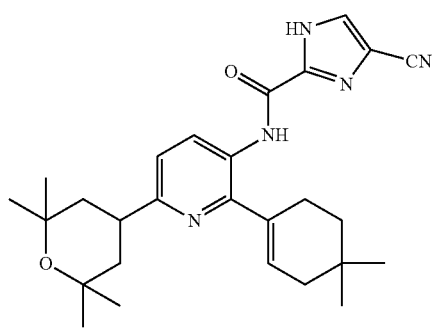

(I-S)

and tautomers, and pharmaceutically acceptable salts thereof (for example, the HCl salt thereof).

Additional embodiments of the present invention, include those wherein the substituents selected for one or more of the variables defined herein (i.e. W, J, X, Z, $R^2$, etc.) are independently selected to be any individual substituent or any subset of substituents selected from the complete list as defined herein.

As used herein, the term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

As used herein, the term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

As used herein, the term "alkylamino" refers to an amino with one alkyl substituent, wherein the amino group is the point of attachment to the rest of the molecule.

As used herein, the term "heteroaryl" refers to 5- to 7-membered mono- or 8- to 10-membered bicyclic aromatic ring systems, any ring of which may contain from one to four heteroatoms selected from N, O and S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

As used herein, the term "heteroatom" refers to a nitrogen atom, an oxygen atom or a sulfur atom wherein the nitrogen and sulfur atoms can exist in any allowed oxidation states.

As used herein, the term "alkoxy" refers to straight or branched chain radicals of up to 12 carbon atoms, unless otherwise indicated, bonded to an oxygen atom. Examples include methoxy, ethoxy, propoxy, isopropoxy and butoxy.

As used herein, the term "spiro-substituted cycloalkenyl" refers to a pair of cycloalkyl rings that share a single carbon atom and wherein at least one of the rings is partially unsaturated, for example:

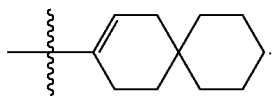

The pharmaceutically-acceptable salts of the compounds of formula (I) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

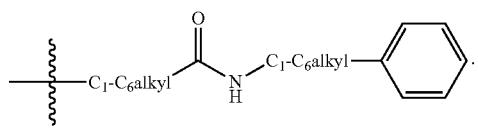

Abbreviations used in the specification, particularly the Schemes and Examples, are as follows:
BINAP=2,2'-Bis-(diphenylphosphino)-1,1'-binaphthyl
DBU=1,8-Diazabicycloundec-7-ene
DME=1,2-Dimethoxyethane
DMSO=Dimethylsulfoxide
dppf=1,1'-Bis(diphenylphosphino)ferrocene HPLC=High Performance Liquid Chromatography
IPA=Isopropyl Alcohol
KOAc=Potassium Acetate
LC=Liquid Chromatography
LDA=Lithium Diisopropylamide
Me=Methyl (i.e. —CH$_3$)
2-methyl-THF=2-Methyl-tetrahydrofuran or 2-Me-THF
MOM=Methoxymethyl ether
NORIT A-SUPRA=Powdered activated carbon available from NORIT America Inc.
NsulphF=1,1,1,2,2,3,3,4,4-nonafluoro-1-butanesulfonyl fluoride
Pd$_2$(OAc)$_2$=Palladium(II)acetate
Pd$_2$(dba)$_3$=Tris(dibenzylidene acetone)dipalladium(0)
Pd(dppf)Cl$_2$=[1,1'-Bis(diphenylphosphino)ferrocene]palladium(II) dichloride
PPh$_3$=Triphenylphosphine
SEM=2-(Trimethylsilyl)ethoxymethyl
TEA=Triethylamine
THF=Tetrahydrofuran
THP=Tetrahydropyranyl
XantPhos=4,5-Bis(diphenylphosphino)-9,9-dimethylxanthene As used herein, unless otherwise noted, the term "isolated form" shall mean that the compound is present in a form which is separate from any solid mixture with another compound(s), solvent system or biological environment. In an embodiment, the present invention is directed to a process for the prepared of the compound of formula (I), preferably the compound of formula (I-S) in an isolated form. In another embodiment, the present invention is directed to a product prepared according to any of the processes as described herein, wherein the product is prepared in an isolated form.

As used herein, unless otherwise noted, the term "substantially pure form" shall mean that the mole percent of impurities in the isolated compound is less than about 5.0 mole percent, preferably less than about 2.0 mole percent, more preferably, less than about 0.5 mole percent, most preferably, less than about 0.1 mole percent. In an embodiment, the present invention is directed to a process for the prepared of the compound of formula (I), preferably the compound of formula (I-S) as a substantially pure form. In another embodiment, the present invention is directed to a product prepared according to any of the processes as described herein, wherein the product is prepared as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5.0 mole percent, preferably less than about 2.0 mole percent, more preferably, less than about 0.5 mole percent, most preferably less than about 0.1 mole percent. In an embodiment, the present invention is directed to a process for the prepared of the compound of formula (I), preferably the compound of formula (I-S) substantially free of corresponding salt form(s). In another embodiment, the present invention is directed to a product prepared according to any of the processes as described herein, wherein the product is prepared in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including, but not limited to, approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows:

$$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-max}]) \times 100.$$

Processes of the Present Invention

The present invention is directed to a process for the preparation of a compound of formula (I), as outlined in Scheme 1, below.

Scheme 1

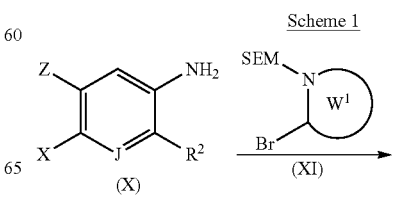

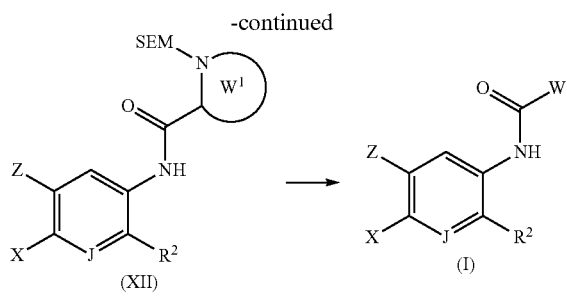

Accordingly, a suitably substituted compound of formula (X), a known compound or compound prepared by known methods, is reacted with a suitably substituted compound of formula (XI) or mixture of SEM protected region-isomers thereof, wherein

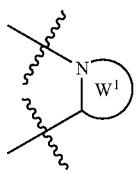 [SMILES: *CN*]

is selected from the group consisting of

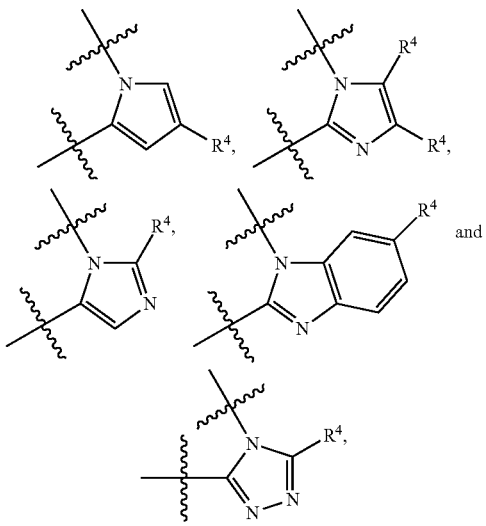

a known compound or compound prepared by known methods;

in the presence of carbon monoxide gas or a source of carbon monoxide, wherein the source of carbon monoxide is for example, a metal carbonyl such as tungsten hexacarbonyl, molibdinum hexacarbonyl, and the like; preferably in the presence of carbon monoxide gas; wherein the carbon monoxide gas is preferably present at a pressure in the range of from about 3.0 bar to about 5.0 bar, more preferably at a pressure in the range of from about 3.0 bar to about 4.0 bar, more preferably at a pressure of about 4.0 bar; (preferably the compound of formula (X) is reacted with the compound of formula (XI) under a carbon monoxide atmosphere);

in the presence of a suitably selected organic or inorganic base such as $K_3PO_4$, $K_2CO_3$, DBU, TEA, pyridine, and the like, preferably an inorganic base such as $K_3PO_4$, $K_2CO_3$, and the like, more preferably, $K_3PO_4$; wherein the base is preferably present in an amount in the range of from about 1.0 to about 2.0 molar equivalents (relative to the moles of the compound of formula (X)), more preferably in an amount in the range of from about 1.5 to about 4.0 molar equivalents, more preferably in an amount in the range of from about 2.0 to about 3.0 molar equivalents;

in the presence of a suitably selected coupling system comprising a suitably selected palladium compound as such as $Pd(OAc)_2$, $Pd_2(dba)_3$, and the like, preferably $Pd(OAc)_2$, and a suitably selected ligand such as XantPhos, BINAP, and the like, preferably XantPhos; more preferably, a mixture of $Pd(OAc)_2$ and XantPhos, more preferably a 1:1 (molar) mixture of $Pd(OAc)_2$ and XantPhos;

wherein the palladium compound is preferably present in an amount of in the range of from about 1.0 mol % (i.e. 0.01 molar equivalents relative to the moles of the compound of formula (X)) to about 4.0 mol %, more preferably in an amount in the range of from about 2.0 mol % to about 3.0 mol %; and wherein the ligand is preferably present in an amount of in the range of from about 1.0 mol % (i.e. 0.01 molar equivalents relative to the moles of the compound of formula (X)) to about 4.0 mol %, more preferably in an amount in the range of from about 2.0 mol % to about 3.0 mol %;

in a suitably selected organic solvent such as toluene, xylene, and the like, preferably toluene; at a temperature in the range of from about 60° C. to about 120° C., more preferably at a temperature in the range of form about 75° C. to about 100° C., more preferably at a temperature of about 90° C.; to yield the corresponding compound of formula (XII).

The compound of formula (XII) is de-protected according to known methods, to yield the corresponding compound of formula (I). For example, the compound of formula (XII) may be de-protected by reacting with a suitably selected acid such as HCl, $H_2SO_4$, and the like, in a suitably selected organic solvent such as isopropanol, ethanol, water, and the like, to yield the corresponding compound of formula (I) or pharmaceutically acceptable salt thereof.

One skilled in the art will readily recognize that when

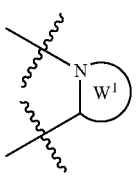 [SMILES: *CN*]

is other than

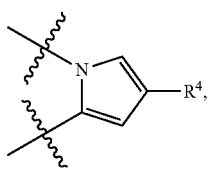

then the compound of formula (XI) may exist as a mixture of its corresponding SEM-protected regioisomers. More particularly, when

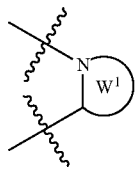

is

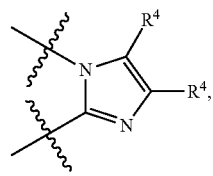

then the mixture of SEM-protected regioisomers of the compound of formula (XI) is a mixture of a compound of formula (XI-R2) and a compound of formula (XI-R3)

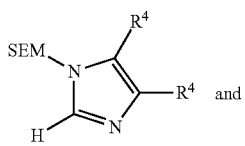 (XI-R2)

and

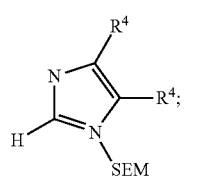 (XI-R3)

when

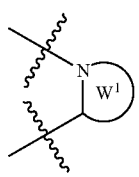

is

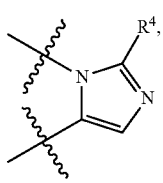

then the mixture of SEM-protected regioisomers of the compound of formula (XI) is a mixture of a compound of formula (XI-R4) and a compound of formula (XI-R5)

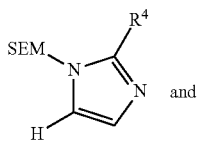 (XI-R4)

and

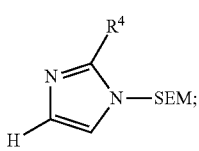 (XI-R5);

when

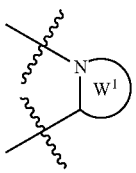 [SMILES: *CN*]

is

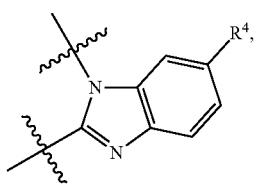

then the mixture of SEM-protected regioisomers of the compound of formula (XI) is a mixture of the following compounds of formula (XI-R6) and a compound of formula (XI-R7)

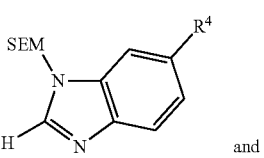 (XI-R6)

and

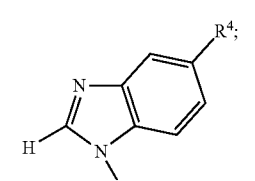 (XI-R7);

and when

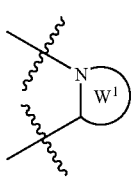 [SMILES: *CN*]

is

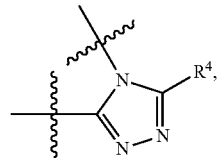

then the mixture of SEM-protected regioisomers of the compound of formula (XI) is a mixture of two or three of a compound of formula (XI-R8), a compound of formula (XI-R9) and/or a compound of formula (XI-R10)

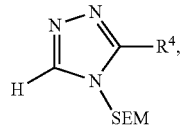
(XI-R8)

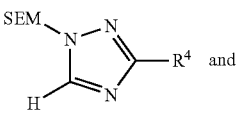
(XI-R9)

and

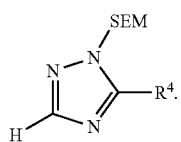
(XI-R10)

One skilled in the art will further readily recognize that the compound of formula (X) may be reacted with a mixture of SEM-protected regioisomers of the compounds of formula (XI) as described above, according to the process as described in Scheme 1, to yield the corresponding compound of formula (XIII).

In an embodiment, the present invention is directed to a process for the preparation of a compound of formula (I-S), as outlined in Scheme 2, below.

Scheme 2

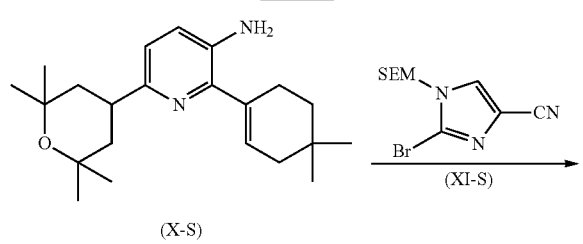
(X-S)

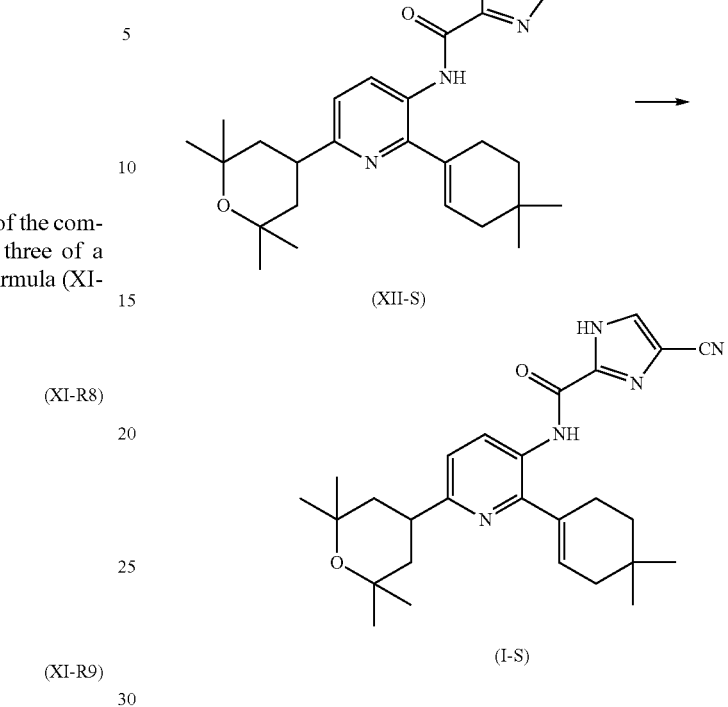
(XII-S)

(I-S)

Accordingly, a suitably substituted compound of formula (X-S), a known compound or compound prepared by known methods, is reacted with a suitably substituted compound of formula (XI-S), a known compound or compound prepared by known methods;

in the presence of carbon monoxide gas or a source of carbon monoxide, wherein the source of carbon monoxide is for example, a metal carbonyl such as tungsten hexacarbonyl, molibdinum hexacarbonyl, and the like; preferably in the presence of carbon monoxide gas; wherein the carbon monoxide gas, preferably at a pressure in the range of from about 3.0 bar to about 5.0 bar, more preferably at a pressure in the range of from about 3.0 bar to about 4.0 bar, more preferably at a pressure of about 4.0 bar; (preferably the compound of formula (X) is reacted with the compound of formula (XI) under a carbon monoxide atmosphere);

in the presence of a suitably selected organic or inorganic base such as $K_3PO_4$, $K_2CO_3$, DBU, TEA, pyridine, and the like, preferably an inorganic base such as $K_3PO_4$, $K_2CO_3$, and the like, more preferably, $K_3PO_4$; wherein the base is preferably present in an amount in the range of from about 1.0 to about 2.0 molar equivalents (relative to the moles of the compound of formula (X-S)), more preferably in an amount in the range of from about 1.5 to about 4.0 molar equivalents, more preferably in an amount in the range of from about 2.0 to about 3.0 molar equivalents;

in the presence of a suitably selected coupling system comprising a suitably selected palladium compound as such as $Pd(OAc)_2$, $Pd_2(dba)_3$, and the like, preferably $Pd(OAc)_2$, and a suitably selected ligand such as XantPhos, BINAP, and the like, preferably XantPhos; more preferably, a mixture of $Pd(OAc)_2$ and XantPhos, more preferably a 1:1 (molar) mixture of $Pd(OAc)_2$ and XantPhos;

wherein the palladium compound is preferably present in an amount of in the range of from about 1.0 mol % (i.e. 0.01 molar equivalents relative to the moles of the compound of formula (X-S)) to about 4.0 mol %, more preferably in an amount in the range of from about 2.0 mol % to about 3.0 mol %; and wherein the ligand is preferably present in an amount of in the range of from about 1.0 mol % (i.e. 0.01 molar equivalents relative to the moles of the compound of formula (X-S)) to about 4.0 mol %, more preferably in an amount in the range of from about 2.0 mol % to about 3.0 mol %;

in a suitably selected organic solvent such as toluene, xylene, and the like, preferably toluene; at a temperature in the range of from about 60° C. to about 120° C., more preferably at a temperature in the range of form about 75° C. to about 100° C., more preferably at a temperature of about 90° C.; to yield the corresponding compound of formula (XII-S).

The compound of formula (XII-S) is de-protected according to known methods, to yield the corresponding compound of formula (I-S). For example, the compound of formula (XII-S) may be de-protected by reacting with a suitably selected acid such as HCl, $H_2SO_4$, and the like, in a suitably selected organic solvent such as isopropanol, ethanol, water, and the like, to yield the corresponding compound of formula (I-S) or pharmaceutically acceptable salt thereof.

In an embodiment, the present invention is directed to a process for the preparation of a compound of formula (I-S), wherein the compound of formula (X-S) is reacted, according to the process described in Scheme 2 above, with a mixture of a compound of formula (XIII-S) and compound of formula (XIV-S)

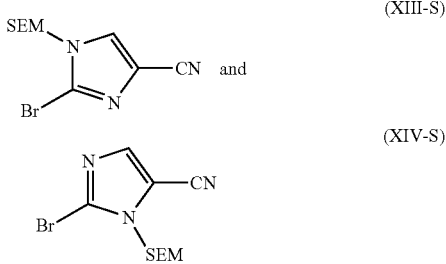

to yield the corresponding compound of formula (I-S).

In another embodiment, the compound of formula (X-S) is reacted with a mixture of a compound of formula (XIII-S) and a compound of formula (XIV-S);

in the presence of carbon monoxide gas or a source of carbon monoxide, wherein the source of carbon monoxide is for example, a metal carbonyl such as tungsten hexacarbonyl, molibdinum hexacarbonyl, and the like; preferably in the presence of carbon monoxide gas; wherein the carbon monoxide gas, preferably at a pressure in the range of from about 3.0 bar to about 5.0 bar, more preferably at a pressure in the range of from about 3.0 bar to about 4.0 bar, more preferably at a pressure of about 4.0 bar; (preferably the compound of formula (X) is reacted with the compound of formula (XI) under a carbon monoxide atmosphere);

in the presence of a suitably selected organic or inorganic base such as $K_3PO_4$, $K_2CO_3$, DBU, TEA, pyridine, and the like, preferably an inorganic base such as $K_3PO_4$, $K_2CO_3$, and the like, more preferably, $K_3PO_4$; wherein the base is preferably present in an amount in the range of from about 1.0 to about 2.0 molar equivalents (relative to the moles of the compound of formula (X-S)), more preferably in an amount in the range of from about 1.5 to about 4.0 molar equivalents, more preferably in an amount in the range of from about 2.0 to about 3.0 molar equivalents;

in the presence of a suitably selected coupling system comprising a suitably selected palladium compound as such as $Pd(OAc)_2$, $Pd_2(dba)_3$, and the like, preferably $Pd(OAc)_2$, and a suitably selected ligand such as XantPhos, BINAP, and the like, preferably XantPhos; more preferably, a mixture of $Pd(OAc)_2$ and XantPhos, more preferably a 1:1 (molar) mixture of $Pd(OAc)_2$ and XantPhos;

wherein the palladium compound is preferably present in an amount of in the range of from about 1.0 mol % (i.e. 0.01 molar equivalents relative to the moles of the compound of formula (X-S)) to about 4.0 mol %, more preferably in an amount in the range of from about 2.0 mol % to about 3.0 mol %; and wherein the ligand is preferably present in an amount of in the range of from about 1.0 mol % (i.e. 0.01 molar equivalents relative to the moles of the compound of formula (X-S)) to about 4.0 mol %, more preferably in an amount in the range of from about 2.0 mol % to about 3.0 mol %;

in a suitably selected organic solvent such as toluene, xylene, and the like, preferably toluene; at a temperature in the range of from about 60° C. to about 120° C., more preferably at a temperature in the range of form about 75° C. to about 100° C., more preferably at a temperature of about 90° C.; to yield the corresponding compound of formula (XII-S).

The compound of formula (XII-S) is de-protected according to known methods, preferably be reacting with a suitably selected acid such as HCl, $H_2SO_4$, and the like, in a suitably selected organic solvent such as isopropanol, ethanol, water, and the like, to yield the corresponding compound of formula (I-S) or pharmaceutically acceptable salt thereof.

The present invention is further directed to an improved process for the preparation of a compound of formula (XX) (useful as an intermediate in the synthesis of pharmaceutical agents), as described in Scheme 3, below.

Scheme 3

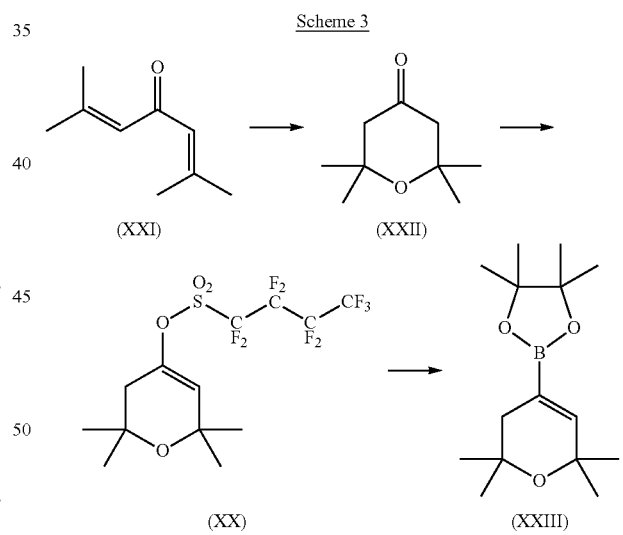

Accordingly, a compound of formula (XXI), a known compound also known as 2,6-dimethylhepta-2,5-dien-4-one, is reacted with a suitably selected acid such as HCl, $H_2SO_4$, HBr and the like, preferably HCl, more preferably 3N HCl; wherein the acid is preferably present in an amount in the range of form about 1.0 to about 5.0 molar equivalents (relative to the moles of the compound of formula (XXI)), more preferably in an amount in the range of about 2.0 to about 4.0 molar equivalents, more preferably in an amount of about 3.0 to about 3.25 molar equivalents; in a suitably selected organic solvent such as methanol, ethanol, isopropanol, and the like, preferably methanol; at a temperature in the range of form about room temperature to about 45° C., more preferably at about 30° C.; to yield the corresponding compound of formula (XXII), also known as 2,2,6,6-tetramethyldihydro-2H-pyran-4(3H)-one.

The compound of formula (XXII) is reacted with NfsulphF, a known compound (also known as 1,1,2,2,3,3,4,4,4-nonafluoro-1-butanesulfonyl fluoride); wherein the NfsulphF is preferably present in an amount in the range of from about 1.0 to about 1.5 molar equivalents (relative to the moles of the compound of formula (XXII)), more preferably in an amount in the range of form about 1.1 to about 1.3 molar equivalents, more preferably in an amount of about 1.2 molar equivalents;

in the presence of DBU; wherein the DBU is preferably present in an amount in the range of from about 1.1 to about 4.0 molar equivalents (relative to the moles of the compound of formula (XXII)), more preferably in an amount in the range of form about 1.5 to about 2.5 molar equivalents, more preferably in an amount of about 2.0 molar equivalents;

in a suitably selected organic solvent such as 2-methyl-THF, THF, toluene, and the like, preferably 2-methyl-THF; at a temperature in the range of from about 0° C. to about room temperature, preferably at about room temperature; to yield the corresponding compound of formula (XX), also known as 2,2,6,6-tetramethyltetrahydro-2H-pyran-4-yl 1,1,2,2,3,3,4,4,4-nonafluorobutane-1-sulfonate.

The process of the present invention for the preparation of a compound of formula (XX) (more particularly the reaction of a compound of formula (XXII) to yield the corresponding compound of formula (XX) as described above) is improved over previously disclosed processes. In the process of the present invention, the use of DBU rather than LDA was unexpectedly found to allow the reaction to proceed at a temperature in the range of from about 0° C. to about room temperature (versus about −78° C. for LDA), which lower temperature is advantageous and/or preferred for large scale manufacture and/or for safety. The process of the present invention for the preparation of the compound of formula (XX) as described above further eliminates the use of methanol (or similarly alcohol), and increases product yield.

The compound of formula (XX) may be further, optionally reacted with diboron pinacol ester (also known as pinacol diborane), a known compound; wherein the diboron pinacol ester is preferably present in an amount in the range of from about 1.0 to about 3.0 molar equivalents (relative to the moles of the compound of formula (XX)), more preferably in an amount in the range of from about 1.05 to about 1.5 molar equivalents, more preferably in an amount of about 1.1 molar equivalents;

in the presence of a suitably selected coupling system comprising a palladium compound and ligand, such as Pd(dppf)Cl$_2$ in a mixture with dppf, Pd(OAc)$_2$ in a mixture with PPh$_3$, and the like; wherein the palladium compound (preferably Pd(dppf)Cl$_2$) is preferably present in an amount in the range of from about 0.01 to about 0.05 molar equivalents (i.e. in an amount in the range of from about 1.0 mol % to about 5.0 mol %), more preferably in an amount in the range of from about 0.02 to about 0.03 molar equivalents (i.e. in an amount in the range of from about 2.0 mol % to about 3.0 mol %), more preferably in an amount of about 0.027 molar equivalents (i.e. in an amount of about 2.7 mol %); and wherein the ligand (preferably, dppf) is preferably present in an amount in the range of from about 0.01 to about 0.05 molar equivalents (i.e. in an amount in the range of from about 1.0 mol % to about 5.0 mol %), more preferably in an amount in the range of from about 0.02 to about 0.03 molar equivalents (i.e. in an amount in the range of from about 2.0 mol % to about 3.0 mole percent), more preferably in an amount of about 0.029 molar equivalents (i.e. in an amount of about 2.9 mol %);

in the presence of a inorganic base such as KOAc, Cs$_2$CO$_3$, and the like; wherein the inorganic base is preferably present in an amount in the range of from about 1.0 to about 5.0 molar equivalents (relative to the moles of the compound of formula (XX)), more preferably in an amount in the range of from about 2.0 to about 4.0 molar equivalents, more preferably in an amount of about 3.0 molar equivalents;

in a suitably selected organic solvent such as DME, toluene, and the like, preferably DME; at a temperature in the range of from about 60° C. to about 100° C., preferably at a temperature of about 80° C.; to yield the corresponding compound of formula (XXIII), also known as 4,4,5,5-tetramethyl-2-(2,2,6,6-tetramethyltetrahydro-2H-pyran-4-yl)-1,3,2-dioxaborolane.

One skilled in the art will recognize that the compound of formula (XXIII) is a reactive species, useful as an intermediate in the synthesis of pharmaceutical compounds, for example, as described in Illig, C., et al., US Patent Publication US 2009/0105296 A1.

The present invention further comprises pharmaceutical compositions containing one or more compounds of formula (I), prepared as described herein, with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15.0 mg/kg/day, or any amount or range therein, preferably from about 0.1 mg/kg/day to about 10.0 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating c-FMS kinase mediated disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by c-FMS kinase is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.1 to about 50.0 mg/kg of body weight per day, or any amount or range therein. More preferably, from about 0.5 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like. One skilled in the art will further recognize that in the Examples which follow, the term "rag-layer" refers to the emulsion which may form between the organic and aqueous layers during separation work-up.

Example 1

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

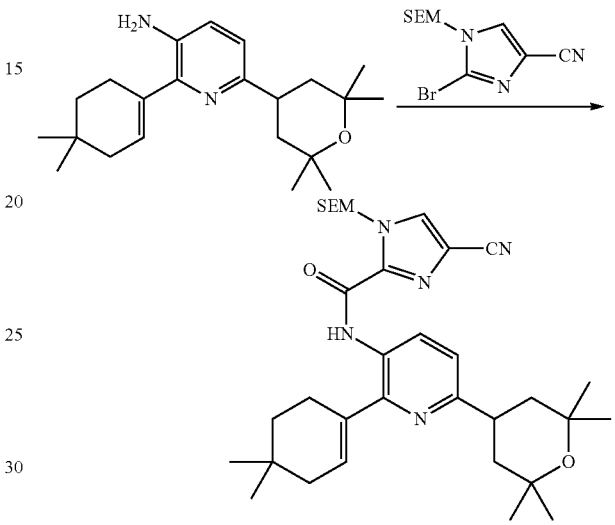

A 60 mL stainless steel MULTIMAX reactor was charged with 2-bromo-1-((2-(trimethylsilyl)ethoxy)methyl)-1H-imidazole-4-carbonitrile (3.26 g, 10.79 mmol, 1.20 equiv), 2-(4,4-dimethylcyclohex-1-en-1-yl)-6-(2,2,6,6-tetramethyltetrahydro-2H-pyran-4-yl)pyridin-3-amine (3.08 g, 8.99 mmol, 1.0 equiv), toluene (28 mL, 24.39 g), DBU (4.10 mL, 4.15 g, 27.28 mmol), XantPhos (155.0 mg, 0.27 mmol) and Pd(OAc)$_2$ (60.0 mg, 0.27 mmol). The reactor was closed, flushed three times with carbon monoxide, and then heated to 90° C. with 2 bar CO present. Carbon monoxide was introduced into the reactor at a pressure of 3 bar and then increased to 4 bar, with the reaction mixture stirring at 750 rpm. The reaction was allowed to proceed with GC monitoring. After 24 hours at 70° C., the reaction mixture was cooled to room temperature.

LC Purity(Area % product/Area % starting material+product+aniline)=90%

Water (20 mL) was added, resulting in some gas formation. The reaction mixture was transferred to an Erlemeyer flask and stirred for 20 minutes. The resulting layers were separated. The organic layer was washed three times with water, filtered and evaporated at 50° C. on a rotovap to yield a dark brown residue. Methanol (18 mL) was added to the residue and the resulting mixture heated to 55° C. Water (1.6 mL) was added and the turbid mixture seeded, resulting in the start of precipitation. The resulting mixture was stirred for 30 min, cooled to room temperature, then placed in a 5° C. ice-water bath, with stirring, for 15 minutes. The resulting mixture was filtered, the solids washed with 5:1 methanol:water mixture, then dried overnight in a vacuum oven at 50° C., to yield the title compound (3.15 g, 5.32 mmol).

Yield: 59.2% (HPLC purity: 97%)

Example 2

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

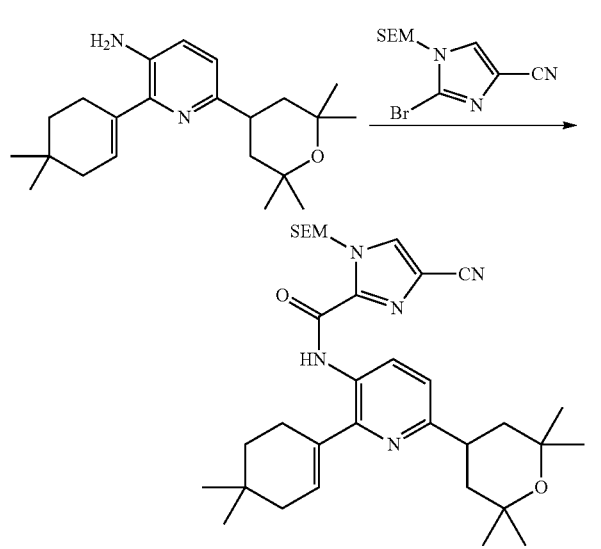

A 60 mL stainless steel MULTIMAX reactor was charged with 2-bromo-1-((2-(trimethylsilyl)ethoxy)methyl)-1H-imidazole-4-carbonitrile (2.97 g, 9.83 mmol, 1.08 equiv), 2-(4,4-dimethylcyclohex-1-en-1-yl)-6-(2,2,6,6-tetramethyltetrahydro-2H-pyran-4-yl)pyridin-3-amine (3.11 g, 9.08 mmol, 1.0 equiv), toluene (27 mL, 23.52 g), potassium phosphate, tribasic, N-hydrate (5.88 g, 26.29 mmol), XantPhos (142.0 mg, 0.25 mmol) and Pd(OAc)$_2$ (54.0 mg, 0.24 mmol). The reactor was closed, flushed three times with nitrogen, and then heated to 90° C. Carbon monoxide was introduced into the reactor at a pressure of 4 bar, with the reaction mixture stirring at 750 rpm. The reaction was allowed to proceed with LC monitoring. The reaction mixture was stirred for a total of 22.5 hours, then cooled to 25° C.

LC Purity(Area % product/Area % starting material+product+aniline)=86%

Water (15 mL) was added, resulting in a temperature increase and formation of foam. The resulting biphasic mixture was stirred for 30 minutes, then the resulting layers were separated. The organic layer was washed three times with water (15 mL), with the pH of the last aqueous layer measured at between pH7 and pH8. The rag-layer was discarded, the organic layer was filtered, then evaporated to yield a residue. Methanol (18 mL) was added to the residue and the resulting mixture heated to 55° C. Water (2.6 mL) was added and the turbid mixture seeded, resulting in the start of crystallization. After a few moments, additional water (1 mL) was added, the resulting mixture cooled to room temperature, then to 2° C. The resulting mixture was filtered, the solids washed with 1:1 methanol:water mixture, then dried overnight to yield the title compound (3.59 g, 6.07 mmol).

Yield: 66.8% (HPLC purity: 96%)

Example 3

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

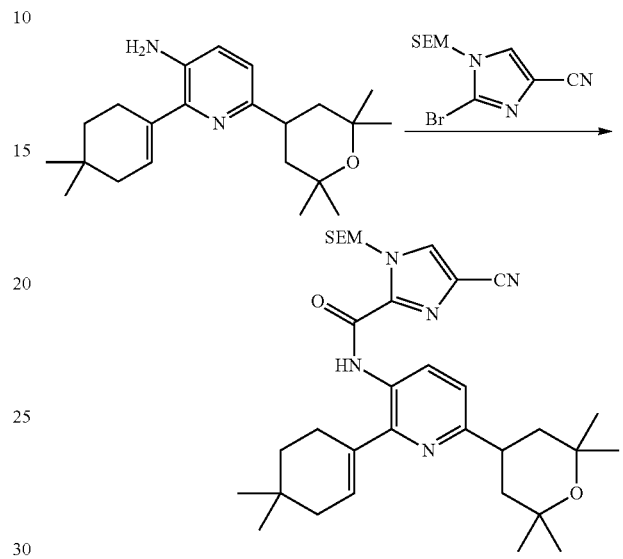

A 60 mL stainless steel MULTIMAX reactor was charged with 2-bromo-1-((2-(trimethylsilyl)ethoxy)methyl)-1H-imidazole-4-carbonitrile (3.80 g, 12.57 mmol, 1.39 equiv), 2-(4,4-dimethylcyclohex-1-en-1-yl)-6-(2,2,6,6-tetramethyltetrahydro-2H-pyran-4-yl)pyridin-3-amine (3.09 g, 9.02 mmol, 1.0 equiv), toluene (27 mL, 23.52 g), potassium phosphate, tribasic, N-hydrate (5.74 g, 27.04 mmol), XantPhos (0.13 g, 0.22 mmol) and Pd(OAc)$_2$ (0.05 g, 0.23 mmol). The reactor was closed, flushed three times with nitrogen, and then heated to 90° C. Carbon monoxide was introduced into the reactor at a pressure of 4 bar, with the reaction mixture stirring at 750 rpm. The reaction was allowed to proceed with LC monitoring. The reaction mixture was stirred overnight (23 hours), then cooled to 25° C.

LC Purity(Area % product/Area % product+aniline)=96%

Water (15 mL) was added, resulting in the observed formation of some gas. The resulting biphasic mixture was transferred to an Erlemeyer flask with magnetic stirred and stirred for 20 minutes. The resulting mixture was filtered, the filter washed with toluene, and the resulting layers were separated. The organic layer was washed three times with water (15 mL). The organic layer was then evaporated to yield a dark brown solid residue. Methanol (18 mL) was added to the residue and the resulting mixture heated to 55° C. Water (1.8 mL) was added, the resulting mixture seeded and allowed to cool to room temperature. The resulting mixture was then cooled 2° C. and stirred for an addition 30 min. The resulting mixture was filtered, the solids washed with 5:1 methanol:water mixture, then dried overnight in a vacuum oven at 50° C. to yield the title compound (4.07 g, 6.88 mmol).

Yield: 76.2% (HPLC purity: 95%)

Example 4

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

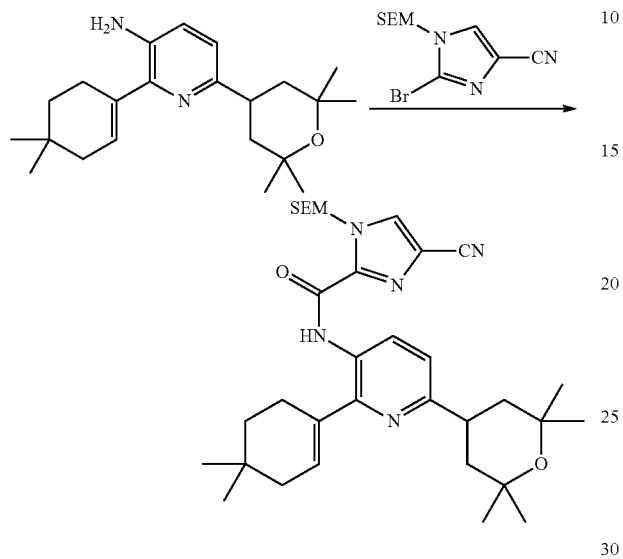

A 60 mL stainless steel MULTIMAX reactor was charged with 2-bromo-1-((2-(trimethylsilyl)ethoxy)methyl)-1H-imidazole-4-carbonitrile (3.26 g, 10.79 mmol, 1.20 equiv), 2-(4,4-dimethylcyclohex-1-en-1-yl)-6-(2,2,6,6-tetramethyltetrahydro-2H-pyran-4-yl)pyridin-3-amine (3.08 g, 8.99 mmol, 1.0 equiv), toluene (27 mL, 23.52 g), potassium phosphate, tribasic, N-hydrate (5.71 g, 26.90 mmol), XantPhos (0.15 g, 0.26 mmol) and Pd(OAc)₂ (0.06 g, 0.27 mmol). The reactor was closed, flushed three times with carbon monoxide, and then heated to 90° C. with 2 bar CO present. Carbon monoxide was introduced into the reactor at a pressure of 4 bar, with the reaction mixture stirring at 750 rpm. The reaction was allowed to proceed with LC monitoring. The reaction was allowed to proceed overnight, then cooled to room temperature.

LC Purity(Area % product/Area % product+aniline)=95%

Water (20 mL) was added, resulting in some gas formation. The reaction mixture was transferred to an Erlemeyer flask and stirred for 20 minutes. The resulting layers were filtered, then washed with toluene, resulting in good separation of the layers. The layers were separated, with almost no rag-layer. The organic layer was filtered and the solvent evaporated on a rotovap at 50° C., to yield a dark brown residue. Methanol (18 mL) was added to the residue and the resulting mixture heated to 50° C. Water (1.6 mL) was added and the resulting mixture seeded, resulting in the start of precipitation. The resulting mixture was stirred while cooling to room temperature, then placed in an ice-water bath, with stirring, for 15 minutes. The resulting mixture was filtered, the solids washed with 5:1 methanol:water mixture, then dried overnight in a vacuum oven at 50° C., to yield the title compound (3.75 g, 6.34 mmol).

Yield: 70.5% (HPLC purity: 95%)

Example 5

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

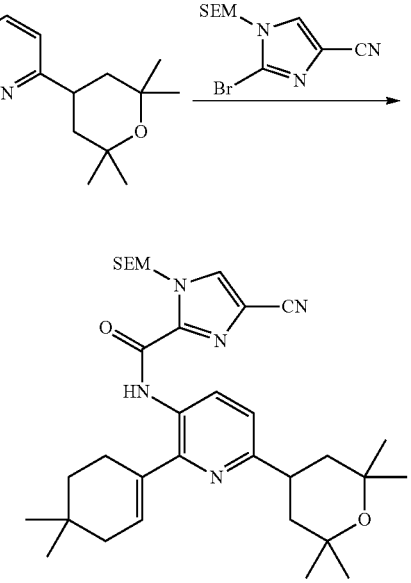

A 60 mL stainless steel MULTIMAX reactor was charged with 2-bromo-1-((2-(trimethylsilyl)ethoxy)methyl)-1H-imidazole-4-carbonitrile (23.58 g, 78.02 mmol, 1.30 equiv), 2-(4,4-dimethylcyclohex-1-en-1-yl)-6-(2,2,6,6-tetramethyltetrahydro-2H-pyran-4-yl)pyridin-3-amine (20.56 g, 60.02 mmol, 1.0 equiv), toluene (242 mL, 210.83 g), potassium phosphate, tribasic, N-hydrate (25.50 g, 120.13 mmol), XantPhos (0.87 g, 1.50 mmol) and Pd(OAc)₂ (0.34 g, 1.51 mmol). The reactor was closed, flushed two times with nitrogen, flushed two times with carbon monoxide, and then heated to 90° C. with 2 bar CO present. Carbon monoxide was introduced into the reactor at a pressure of 4 bar, with the reaction mixture stirring at 750 rpm. The reaction was allowed to proceed with LC monitoring. The reaction was allowed to proceed for 40 hours, then stirred at 4 bar pressure, but without additional CO supply for an additional 44 hrs, then cooled to 20° C.

LC Purity(Area % product/Area % product+bromide)=98%

Water (120 mL) was added, resulting in some gas formation. The reaction mixture was then stirred vigorously for 30 min. The resulting biphasic mixture was filtered and the solids washed with toluene. The layers were separated—the colorless aqueous layer had a pH+10, and the dark brown organic layer retained. The organic layer was washed with water (120 mL), the layers separated—the colorless aqueous layer had a pH of ~8, with very little rag-layer. The organic layer was washed a second time with water (120 mL), and the layers separated—the colorless layer had a neutral pH. The retained organic layer was transferred to an 500 mL round bottom flask (RBF) equipped with a Dean-Stark trap and the resulting mixture azeotropically dried at 110° C., removing about 50 mL. The resulting mixture was cooled to 80° C., NORIT A-SUPRA (3.59 g) was added and the resulting mixture heated to 100° C., then stirred for 4 hours. The resulting mixture was then cooled to 60° C., filtered and the solids washed with toluene. The resulting mixture was then transferred to a new RBF, silica gel thiol (9 g) added, the mixture stirred overnight at 90° C., then cooled to room temperature. The resulting dark brown mixture was filtered, and the solids washed with toluene. The resulting mixture was again transferred to a new RBF, silica gel thiol (9 g) added, the mixture stirred overnight at 90° C., then cooled to room temperature. The resulting mixture was filtered, the solids washed with toluene and the solvent evaporated by rotovap to yield a residue. The flask containing the residue was flushed two times with methanol (60 mL). Methanol (150 mL) was added to the residue and the resulting mixture heated to reflux. The resulting mixture was allowed to cool to room temperature, with spontaneous precipitation observed at about 40° C. The resulting mixture was then stirred for 2 hrs at room temperature, filtered, the solids washed twice with methanol (30 mL) and the resulting solids dried in vacuo overnight at 50° C., to yield the title compound (21.05 g, 35.57 mmol).

Yield: 59.2%

Example 6

4-cyano-N-(2-(4,4-dimethylcyclohex-1-en-1-yl)-6-(2,2,6,6-tetramethyltetrahydro-2H-pyran-4-yl)pyridin-3-yl)-1-((2-(trimethylsilyl)ethoxy)methyl)-1H-imidazole-2-carboxamide

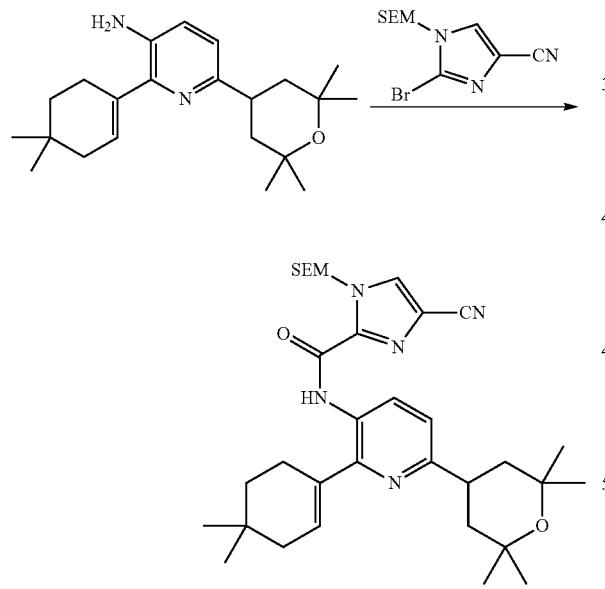

A 60 mL stainless steel MULTIMAX reactor was charged with 2-bromo-1-((2-(trimethylsilyl)ethoxy)methyl)-1H-imidazole-4-carbonitrile (3.28 g, 10.85 mmol, 1.21 equiv), 2-(4,4-dimethylcyclohex-1-en-1-yl)-6-(2,2,6,6-tetramethyltetrahydro-2H-pyran-4-yl)pyridin-3-amine (3.07 g, 8.96 mmol, 1.0 equiv), toluene (27 mL, 23.52 g), potassium carbonate (1.88 g, 13.60 mmol), XantPhos (0.16 g, 0.27 mmol) and Pd(OAc)$_2$ (0.06 g, 0.26 mmol). The reactor was closed, flushed three times with carbon monoxide, and then heated to 90° C., while maintaining carbon monoxide at a pressure of 2.5 bar. Carbon monoxide was introduced into the reactor at a pressure of 4 bar, with the reaction mixture stirring at 750 rpm. The reaction was allowed to proceed with LC monitoring. The reaction mixture was stirred overnight. To the reaction mixture was then added a solution of 2-bromo-1-((2-(trimethylsilyl)ethoxy)methyl)-1H-imidazole-4-carbonitrile (0.65 g) in toluene. The resulting mixture was stirred for an additional 2 hours, sampled and then stirred further, overnight at 90° C. The resulting mixture was then cooled to 25° C. and allowed to stand at room temperature.

LC Purity(Area % product/Area % product+ aniline)=96%

Water (20 mL) was added, and the resulting mixture was then transferred to an Erlemeyer flask stirred for 30 minutes. The resulting mixture was filtered, and the resulting layers were separated. The organic layer was washed three times with water (20 mL). The rag-layer was filtered off. Toluene (50 mL) was added to the organic layer, the resulting mixture transferred to a 250 mL RBF and azeotropically distilled by removing about 50 mL. NORIT A-SUPRA (0.53 g) was added and the resulting mixture stirred at 100° C. for 1.5 hrs. The resulting mixture was filtered, the filter washed with toluene, then transferred to a clean RBF and stirred at for 3 hrs, at 100° C., in the presence of Silica gel thiol (1.04 g). The resulting mixture was cooled to room temperature, then filtered. The reaction mixture was returned to the RBF, then stirred overnight at 90° C. in the presence of Silica gel thiol (1.0 g). The resulting mixture was cooled to room temperature, filtered and the solids washed with toluene. The solvent was evaporated on a rotovap to yield a residue. Methanol (18 mL) was added to the residue and the resulting mixture heated to 55° C. Water (1.8 mL) was added at 50° C., the resulting mixture seeded and then allowed to cool to room temperature, resulting in precipitation of a solid. The resulting mixture was stirred for an additional 2 hrs at room temperature, then filtered. The resulting solids were washed with 5:1 methanol: water mixture, then dried overnight in a vacuum oven at 50° C. to yield the title compound (4.09 g, 6.91 mmol).

Yield: 77.1% (relative HPLC purity 97%)

Example 7

4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide HCl salt

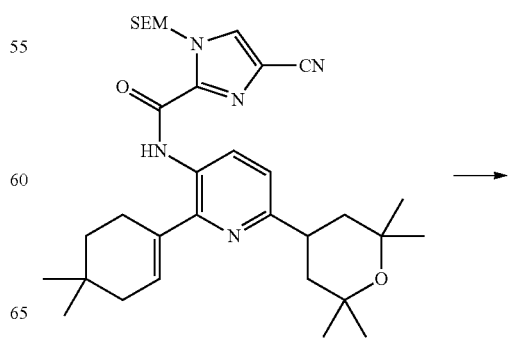

-continued

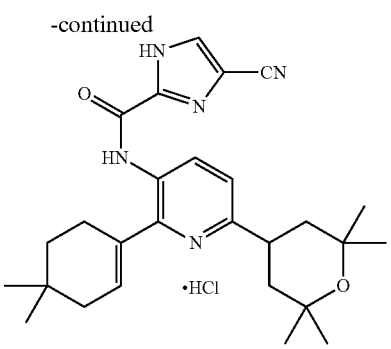

To a 1 L 3-neck round bottom flask equipped with an overhead stirrer, 250 mL addition funnel, argon inlet and heating mantle was added 4-cyano-N-(2-(4,4-di methylcyclohex-1-enyl)-6-(2,2,6,6-tetramethyltetrahydro-1H-pyran-4-yl)pyridine-3-yl)-1-(2-(trimethylsilyl)ethoxy)methyl)-1-imidazole-2-carboxamide (60.5 g, 0.102 mol) followed by 3% aqueous IPA (265 mL). The temperature was set at 65° C., HCl in IPA (~5.5 N, 185 mL) was added dropwise to the mixture at room temperature. After 7 min, an additional portion of HCl-IPA (90 mL) was added, and the internal temperature was 50° C. Addition was complete after 18 min, with the internal temperature at 65° C. The temperature was then increased to 70° C. The de-protection was monitored by HPLC. After 1.5 hours, the heating mantle was removed and the mixture immersed in a dry ice/acetone bath, cooling the reaction to −18° C. After standing in the bath at −10° C. and −18° C. for 30 minutes, the resulting solid precipitate was isolated by filtration. The solids were washed with cold IPA (60 mL) and dried to yield the title compound as a solid (29 g). The mother liquor was diluted with diethyl ether (20 mL) and set in a refrigerator overnight. The resulting mixture was then concentrated to ½ volume, diethyl ether (6 mL) was added and the resulting mixture cooled on dry ice for 30 min. The resulting mixture was filtered to yield the title compound as a solid (7.1 g). The combined solids were dried at 140° C. for 1.5 days in a vacuum oven to yield the title compound.

Yield: 36.1 g, 73%

Example 8

2,2,6,6-tetramethyl-3,6-dihydro-2H-pyran-4-yl 1,1,2,2,3,3,4,4,4-nonafluorobutane-1-sulfonate

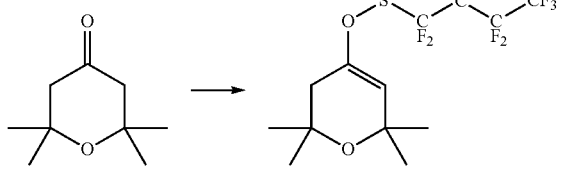

A 2 L RBF under light nitrogen flow was charged with 2,2,6,6-tetramethyldihydro-2H-pyran-4(3H)-one (1.00 equiv; 49.10 mL; 43.45 g), (a known compound which may be prepared as described in, for example, MAGNUS, P., et al., "Synthesis of the ABCD-rings of the insecticidal indole alkaloid nodulisporic acid", *Tet. Lett.*, 1999, pp 6909-6912, Vol. 40) 2-methyl-THF (375.00 mL; 322.05 g) and DBU (76.67 mL; 77.67 g). The resulting mixture was stirred and cooled to about 2° C. with a water-ice bath. NfsulphF (1.20 equiv;

56.07 mL; 94.20 g) was introduced into a dropping funnel and the NfsulphF was then added to the reaction mixture over 20 minutes, with a light exotherm is observed. After complete addition, the water-ice bath was taken away and the temperature allowed to rise to room temperature. Precipitation was observed to start forming, resulting in a yellow suspension. The yellow suspension was stirred overnight at room temperature and yielded yield a brown suspension.

To the brown suspension was slowly added water (1.12 L; 1.12 kg), with an observed exotherm. The resulting mixture was warmed 44° C., resulting in a multi-phase mixture with good separation (the organic layer was the top layer). The mixture was stirred for 20 minutes and the phases warm separated at about 44° C. The aqueous (orange colored) layer was returned to the RBF, and then extracted with 2-methyl-THF (185.00 mL; 158.88 g) by stirring 20 minutes at 44° C., then warm separating the resulting layers. The organic layers were then combined. Water (190.00 mL; 190.00 g) was added and the resulting mixture stir for 20 minutes, and the resulting layers warm separated at 44° C. The organic layer was then washed second time with water (190.00 mL; 190.00 g), with some white fluffy precipitation observed in the water layer. The organic layer was then evaporated on a rotavap at 45° C. The resulting biphasic residue included a thick brown bottom layer (129.17 g) and light colored material on top. To the residue was added HEPTANE 50% (a mixture of 50% n-heptane, 20% other heptane isomers and 30% methyl cyclohexane; 250.00 mL; 176.75 g), then acetonitrile (19.00 mL; 14.88 g). The resulting mixture was stirred firmly, the acetonitrile was observed to take up the oily layer, resulting in a biphasic system. The mixture was then stirred for 1 hour, the layers separated. The heptane layer was evaporated on a rotavap at 42° C. to yield the title compound as a residue (102.60 g)

Actual Yield: 93.52% 102.60 g, 234.08 mmol

Theoretical Yield: 100% 109.58 g, 250.00 mmol

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

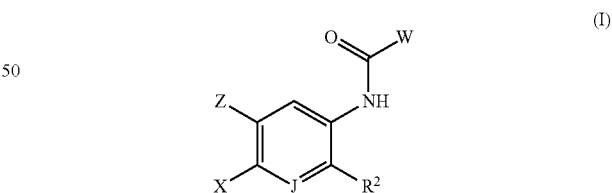

wherein
W is selected from the group consisting of

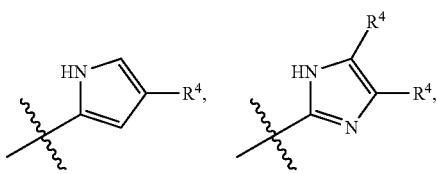

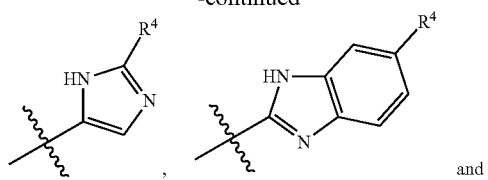

, and

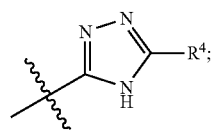

each R⁴ is independently selected from the group consisting of hydrogen, F, Cl, Br, I, —OH, —OCH₃, —OCH₂CH₃, —SC$_{(1-4)}$alkyl, —SOC$_{(1-4)}$alkyl, —SO₂C$_{(1-4)}$alkyl, —C$_{(1-3)}$alkyl, —CO₂R$^d$, —CONR$^e$R$^f$, —CCR$^g$ and —CN;

wherein R$^d$ is selected from the group consisting of H and —C$_{(1-3)}$alkyl; R$^e$ is selected from the group consisting of H and —C$_{(1-3)}$alkyl; R$^f$ is selected from the group consisting of H and —C$_{(1-3)}$alkyl; and R$^g$ is selected from the group consisting of hydrogen, —CH₂OH and —CH₂CH₂OH;

J is selected from the group consisting of CH and N;

R² is selected from the group consisting of cycloalkyl, spiro-substituted cycloalkenyl, thiophenyl, dihydrosulfonopyranyl, phenyl, furanyl, tetrahydropyridyl and dihydropyranyl; any of which may be independently substituted with one or two of each of the following: chloro, fluoro, hydroxy, and C$_{(1-4)}$alkyl;

Z is selected from the group consisting of hydrogen, F, Cl and CH₃;

X is selected from the group consisting of

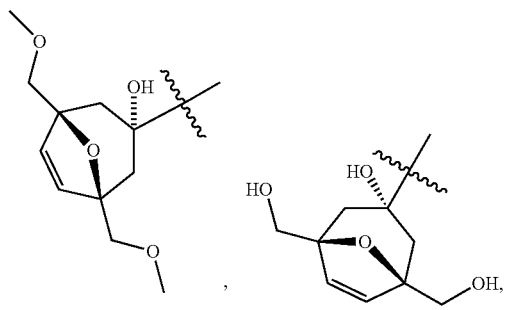

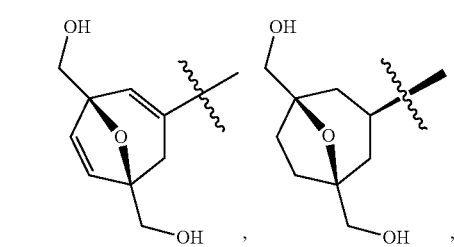

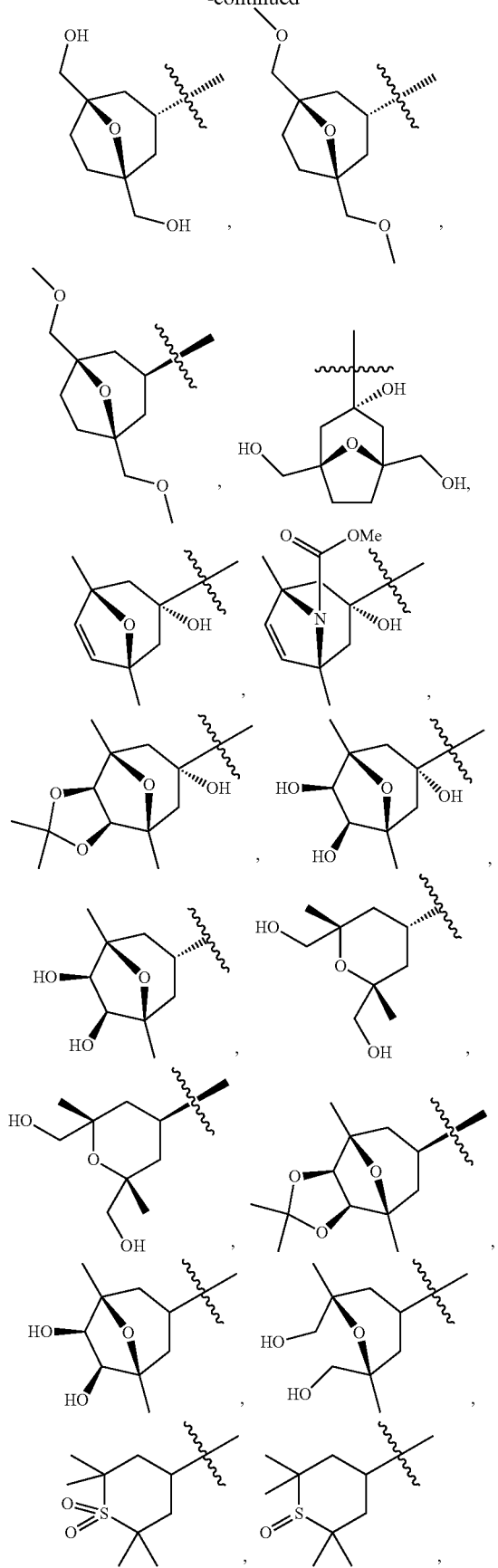

-continued

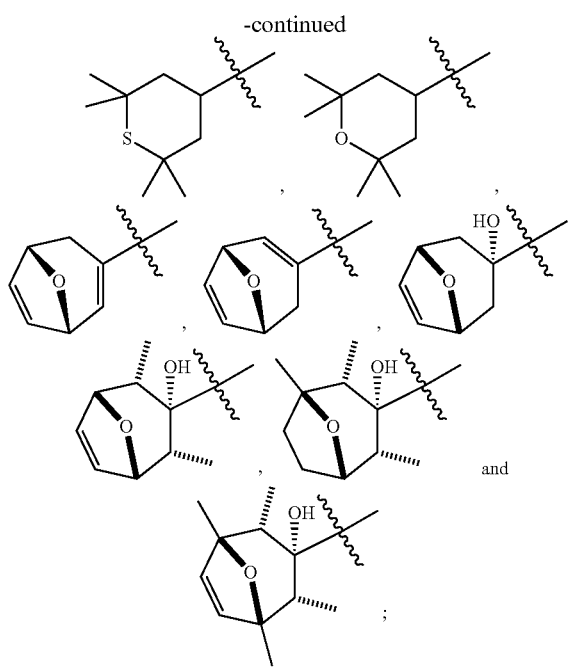

wherein $R^w$ is selected from the group consisting of hydrogen, —$C_{(1-4)}$alkyl, —$CO_2C_{(1-4)}$alkyl, —$CONH_2$, —$CONHC_{(1-4)}$alkyl, —$CON(C_{(1-4)}alkyl)_2$ and —$COC_{(1-4)}$alkyl;

or a tautomer or pharmaceutically acceptable salt thereof; comprising

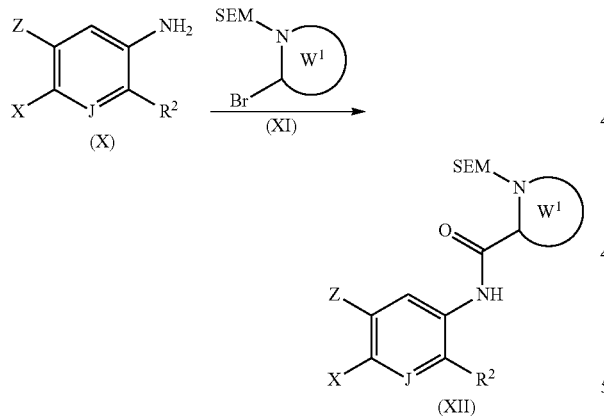

reacting a compound of formula (X) with a compound of formula (XI) or a mixture of SEM protected regionisomers thereof,
wherein

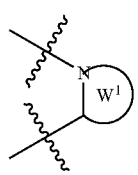 [SMILES: *CN*]

is selected from the group consisting of

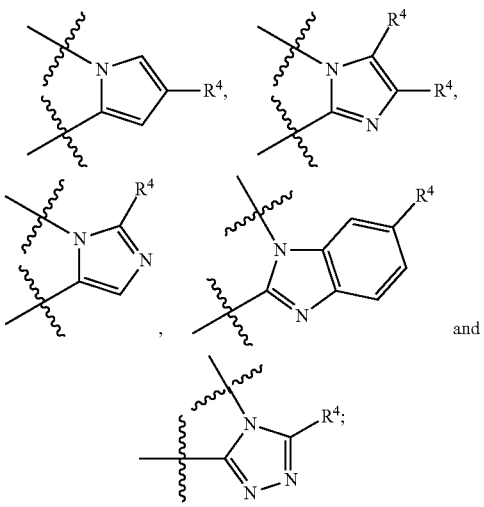

in the presence of carbon monoxide gas or a source of carbon monoxide;

in the presence of an organic or inorganic base;

in the presence of a suitably selected coupling system comprising a palladium compound selected from the group consisting of $Pd(OAc)_2$ and $Pd_2(dba)_3$ and a ligand selected from the group consisting of XantPhos and BINAP;

in an organic solvent;

at a temperature in the range of from about 60° C. to about 120° C.

to yield the corresponding compound of formula (XII);

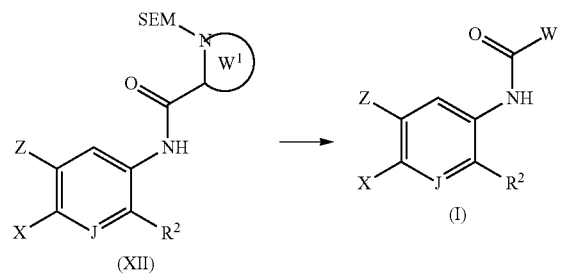

de-protecting the compound of formula (XII), to yield the corresponding compound of formula (I).

2. A process according to claim 1, wherein J is N; Z is hydrogen; X is 2, 2, 6, 6-tetramethyltetrahydro-2H-pyran-4-yl; $R^2$ is 1-(4,4-dimethyl-cyclohex-1-ene); W is 4-cynao-1H-imidazol-2-yl and

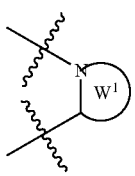 [SMILES: *CN*]

is

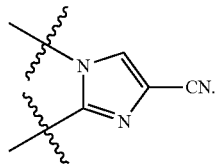 [SMILES: *c1nc(C#N)cn1*]

3. A process according to claim 1, wherein the source of carbon monoxide is a metal carbonyl selected from the group consisting of tungsten hexacarbonyl and molibdinum hexacarbonyl.

4. A process according to claim 1, wherein the compound of formula (X) is reacted with the compound of formula (XI) in the presence of carbon monoxide gas.

5. A process according to claim 4, wherein the carbon monoxide is present at a pressure in the range of from about 3.0 bar to about 5.0 bar.

6. A process according to claim 5, wherein the carbon monoxide is present at a pressure in the range of from about 3.0 bar to about 4.0 bar.

7. A process according to claim 6, wherein the carbon monoxide is present at a pressure of about 4.0 bar.

8. A process according to claim 1, wherein the compound of formula (X) is reacted with the compound of formula (XI) under a carbon monoxide atmosphere.

9. A process according to claim 1, wherein the organic or inorganic base is selected from the group consisting of $K_3PO_4$, $K_2CO_3$, DBU, TEA and pyridine.

10. A process according to claim 1, wherein the organic or inorganic base is an inorganic base.

11. A process according to claim 10, wherein the inorganic base is selected from the group consisting of $K_3PO_4$ and $K_2CO_3$.

12. A process according to claim 10, wherein the inorganic base is $K_3PO_4$.

13. A process according to claim 10, wherein the inorganic base is present in an amount from about 1.0 to about 2.0 molar equivalents.

14. A process according to claim 13, wherein the inorganic base is present in an amount from about 1.5 to about 4.0 molar equivalents.

15. A process according to claim 14, wherein the inorganic base is present in an amount from about 2.0 to about 3.0 molar equivalents.

16. A process according to claim 1, wherein the palladium compound is $Pd(OAc)_2$.

17. A process according to claim 16, wherein the $Pd(OAc)_2$ is present in an amount from about 1.0 mol % to about 4.0 mol %.

18. A process according to claim 17, wherein the $Pd(OAc)_2$ is present in an amount from about 2.0 mol % to about 3.0 mol %.

19. A process according to claim 1, wherein the ligand is XantPhos.

20. A process according to claim 19, wherein the XantPhos is present in an amount from about 1.0 mol % to about 4.0 mol %.

21. A process according to claim 20, wherein the XantPhos is present in an amount from about 2.0 mol % to about 3.0 mol %.

22. A process according to claim 1, wherein the palladium compound is $Pd(OAc)_2$ and wherein the ligand is XantPhos.

23. A process according to claim 22, wherein the $Pd(OAc)_2$ is present in an amount from about 2.0 mol % to about 3.0 mol %; and wherein the XantPhos is present in an amount from about 2.0 mol % to about 3.0 mol %.

24. A process according to claim 1, wherein the coupling system is a 1:1 mixture of a palladium compound and a ligand.

25. A process according to claim 1, wherein the coupling system is a 1:1 mixture of a palladium compound and a ligand;
wherein the palladium compound is $Pd(OAc)_2$; wherein the palladium compound is present in an amount of from about 2.0 mol % to about 3.0 mol %;
wherein the ligand is XantPhos; and wherein the ligand is present in an amount of from about 2.0 mol % to about 3.0 mol %.

26. A process according to claim 1, wherein the organic solvent is toluene.

27. A process according to claim 1, wherein the compound of formula (X) is reacted with the compound of formula (XI) at a temperature of from about 60° C. to about 120° C.

28. A process according to claim 27, wherein the compound of formula (X) is reacted with the compound of formula (XI) at a temperature of from about 75° C. to about 100° C.

29. A process according to claim 28, wherein the compound of formula (X) is reacted with the compound of formula (XI) at a temperature of about 90° C.

30. A process according to claim 1, wherein the compound of formula (XI) is de-protected by reacting the compound of formula (XII) with HCl in isopropanol.

31. A process according to claim 1, wherein the compound of formula (X) is reacted with the compound of formula (XI);
in the presence of carbon monoxide gas; wherein the carbon monoxide gas is present at a pressure in an amount of about 4.0 bar;
wherein the organic or inorganic base is $K_3PO_4$; wherein the $K_3PO_4$ is present in an amount of from about 2.0 molar equivalents to about 3.0 molar equivalents;
wherein the coupling system is a 1:1 mixture of a palladium compound and a ligand; wherein the palladium compound is $Pd(OAc)_2$; wherein the $Pd(OAc)_2$ is present in an amount of from about 2.0 mol % to about 3.0 mol %; wherein the ligand is XantPhos; wherein the XantPhos is present in an amount of from about 2.0 mol % to about 3.0 mol %;
wherein the organic solvent is toluene; and wherein the compound of formula (X) is reacted with the compound of formula (XI) at a temperature of about 90° C.

32. A process according to claim 31, wherein J is N; Z is hydrogen; X is 2, 2, 6, 6-tetramethyltetrahydro-2H-pyran-4-yl; $R^2$ is 1-(4,4-dimethyl-cyclohex-1-ene); W is 4-cynao-1H-imidazol-2-yl and

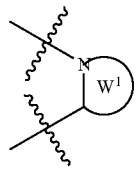 [SMILES: *CN*]

is

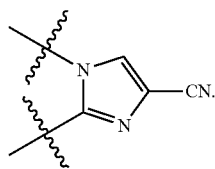 [SMILES: *c1nc(C#N)cn1*]

33. A process for the preparation of a compound of formula (I-S)

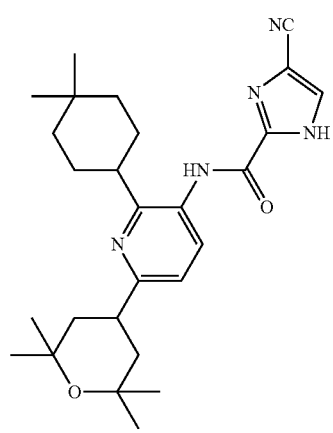
(I-S)

or a tautomer or pharmaceutically acceptable salt thereof; comprising

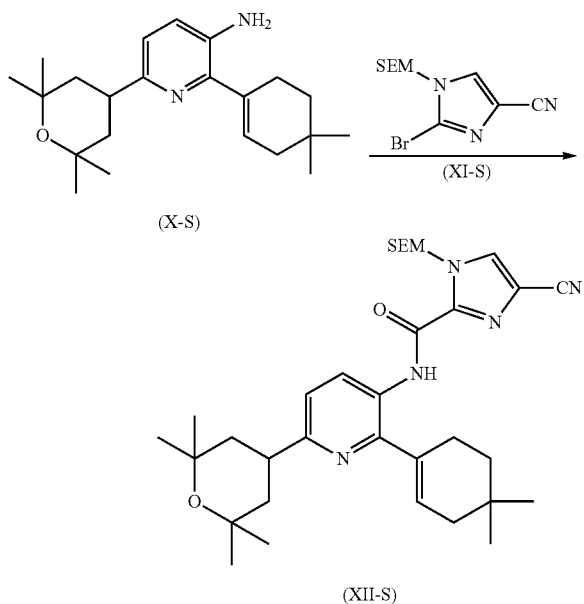

reacting a compound of formula (X-S) with a compound of formula (XI-S);
in the presence of carbon monoxide gas or a source of carbon monoxide;
in the presence of an organic or inorganic base;
in the presence of a suitably selected coupling system comprising a palladium compound selected from the group consisting of Pd(OAc)$_2$ and Pd$_2$(dba)$_3$ and a ligand selected from the group consisting of XantPhos and BINAP;
in an organic solvent;
at a temperature of from about 60° C. to about 120° C. to yield the corresponding compound of formula (XII-S);

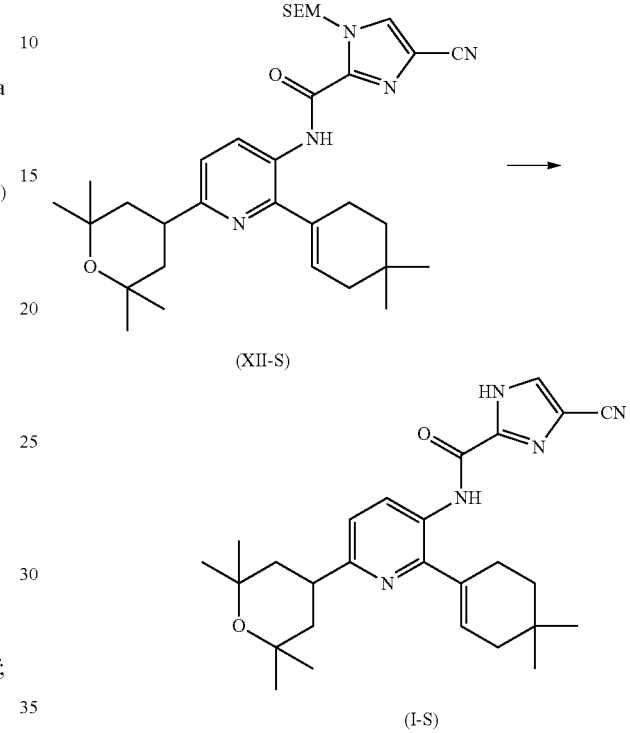

de-protecting the compound of formula (XII-S) to yield the corresponding compound of formula (I-S).

34. A process according to claim 33, wherein the source of carbon monoxide is a metal carbonyl selected from the group consisting of tungsten hexacarbonyl and molibdinum hexacarbonyl.

35. A process according to claim 33, wherein the compound of formula (X) is reacted with the compound of formula (XI) in the presence of carbon monoxide gas.

36. A process according to claim 35, wherein the carbon monoxide is present at a pressure of from about 3.0 bar to about 5.0 bar.

37. A process according to claim 36, wherein the carbon monoxide is present at a pressure of from about 3.0 bar to about 4.0 bar.

38. A process according to claim 37, wherein the carbon monoxide is present at a pressure of about 4.0 bar.

39. A process according to claim 33, wherein the compound of formula (X) is reacted with the compound of formula (XI) under a carbon monoxide atmosphere.

40. A process according to claim 33, wherein the organic or inorganic base is selected from the group consisting of K$_3$PO$_4$, K$_2$CO$_3$, DBU, TEA and pyridine.

41. A process according to claim 33, wherein the organic or inorganic base is an inorganic base.

42. A process according to claim 41, wherein the inorganic base is selected from the group consisting of K$_3$PO$_4$ and K$_2$CO$_3$.

43. A process according to claim 41, wherein the inorganic base is K$_3$PO$_4$.

44. A process according to claim 41, wherein the inorganic base is present in an amount of from about 1.0 to about 2.0 molar equivalents.

45. A process according to claim 44, wherein the inorganic base is present in an amount of from about 1.5 to about 4.0 molar equivalents.

46. A process according to claim 45, wherein the inorganic base is present in an amount of from about 2.0 to about 3.0 molar equivalents.

47. A process according to claim 33, wherein the palladium compound is $Pd(OAc)_2$.

48. A process according to claim 47, wherein the $Pd(OAc)_2$ is present in an amount of from about 1.0 mol % to about 4.0 mol %.

49. A process according to claim 48, wherein the $Pd(OAc)_2$ is present in an amount of from about 2.0 mol % to about 3.0 mol %.

50. A process according to claim 33, wherein the ligand is XantPhos.

51. A process according to claim 50, wherein the XantPhos is present in an amount of from about 1.0 mol % to about 4.0 mol %.

52. A process according to claim 51, wherein the XantPhos is present in an amount of from about 2.0 mol % to about 3.0 mol %.

53. A process according to claim 33, wherein the palladium compound is $Pd(OAc)_2$ and wherein the ligand is XantPhos.

54. A process according to claim 53, wherein the $Pd(OAc)_2$ is present in an amount of from about 2.0 mol % to about 3.0 mol %; and wherein the XantPhos is present in an amount of from about 2.0 mol % to about 3.0 mol %.

55. A process according to claim 33, wherein the coupling system is a 1:1 mixture of a palladium compound and a ligand.

56. A process according to claim 33, wherein the coupling systems is a 1:1 mixture of a palladium compound and a ligand;
wherein the palladium compound is $Pd(OAc)_2$; wherein the palladium compound is present in an amount of from about 2.0 mol % to about 3.0 mol %;
wherein the ligand is XantPhos; and wherein the ligand is present in an amount of from about 2.0 mol % to about 3.0 mol %.

57. A process according to claim 33, wherein the organic solvent is toluene.

58. A process according to claim 33, wherein the compound of formula (X) is reacted with the compound of formula (XI) at a temperature of from about 60° C. to about 120° C.

59. A process according to claim 58, wherein the compound of formula (X) is reacted with the compound of formula (XI) at a temperature of from about 75° C. to about 100° C.

60. A process according to claim 59, wherein the compound of formula (X) is reacted with the compound of formula (XI) at a temperature of about 90° C.

61. A process according to claim 33, wherein the compound of formula (XI) is de-protected by reacting the compound of formula (XII) with HCl in isopropanol.

62. A process according to claim 33, wherein the compound of formula (X) is reacted with the compound of formula (XI);
in the presence of carbon monoxide gas; wherein the carbon monoxide gas is present at a pressure in an amount of about 4.0 bar;
wherein the organic or inorganic base is $K_3PO_4$; wherein the $K_3PO_4$ is present in an amount of from about 2.0 molar equivalents to about 3.0 molar equivalents;
wherein the coupling system is a 1:1 mixture of a palladium compound and a ligand; wherein the palladium compound is $Pd(OAc)_2$; wherein the $Pd(OAc)_2$ is present in an amount of from about 2.0 mol % to about 3.0 mol %; wherein the ligand is XantPhos; wherein the XantPhos is present in an amount of from about 2.0 mol % to about 3.0 mol %;
wherein the organic solvent is toluene; and wherein the compound of formula (X) is reacted with the compound of formula (XI) at a temperature of about 90° C.

* * * * *